(12) United States Patent
Crudden

(10) Patent No.: US 9,034,393 B2
(45) Date of Patent: *May 19, 2015

(54) BIOACTIVE ACID AGRICHEMICAL COMPOSITIONS AND USE THEREOF

(75) Inventor: Joseph J. Crudden, Hudson, NH (US)

(73) Assignee: SCIESSENT LLC, Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,279

(22) Filed: Sep. 14, 2012

(65) Prior Publication Data

US 2013/0004587 A1  Jan. 3, 2013

Related U.S. Application Data

(63) Continuation of application No. 12/154,135, filed on May 19, 2008, now Pat. No. 8,282,949.

(60) Provisional application No. 60/930,913, filed on May 18, 2007.

(51) Int. Cl.
| | |
|---|---|
| *A61K 33/38* | (2006.01) |
| *A61K 33/34* | (2006.01) |
| *A01N 25/26* | (2006.01) |
| *A01N 59/00* | (2006.01) |
| *A01N 59/16* | (2006.01) |
| *A01N 55/02* | (2006.01) |
| *A61K 31/315* | (2006.01) |
| *A61K 31/28* | (2006.01) |
| *A61K 31/30* | (2006.01) |
| *A01N 25/04* | (2006.01) |
| *A01N 25/12* | (2006.01) |
| *A01N 59/20* | (2006.01) |
| *A23L 3/3463* | (2006.01) |
| *A23L 3/3508* | (2006.01) |
| *A23L 3/3526* | (2006.01) |
| *A23L 3/3535* | (2006.01) |
| *A23L 3/358* | (2006.01) |

(52) U.S. Cl.
CPC ............. *A01N 25/04* (2013.01); *A01N 25/12* (2013.01); *A01N 59/16* (2013.01); *A01N 59/20* (2013.01); *A23L 3/3463* (2013.01); *A23L 3/3508* (2013.01); *A23L 3/3526* (2013.01); *A23L 3/3535* (2013.01); *A23L 3/358* (2013.01)

(58) Field of Classification Search
None
See application file for complete search history.

(56) References Cited

U.S. PATENT DOCUMENTS

| | | | |
|---|---|---|---|
| 3,404,987 A | | 10/1968 | Kooistra et al. |
| 4,010,253 A | * | 3/1977 | Reese et al. ............ 424/47 |
| 4,797,274 A | | 1/1989 | Miki et al. |
| 2002/0025344 A1 | * | 2/2002 | Newman et al. ......... 424/618 |
| 2003/0206965 A1 | | 11/2003 | Hasan et al. |
| 2005/0227895 A1 | | 10/2005 | Ghosh et al. |
| 2008/0317800 A1 | * | 12/2008 | Amirzadeh-Asl ......... 424/405 |

FOREIGN PATENT DOCUMENTS

| | | |
|---|---|---|
| WO | 9800012 A1 | 1/1998 |
| WO | 9953760 A1 | 10/1999 |
| WO | 02060248 A2 | 8/2002 |
| WO | 02096202 A1 | 12/2002 |
| WO | 03028455 A1 | 4/2003 |
| WO | 2005023022 A1 | 3/2005 |

OTHER PUBLICATIONS

Database WPI Week 200444 Thomson Scientific, London, GB; AN 2004-464537 XP002493414 & JP 2004 175686 A (KAO Corp) Jun. 24, 2004.

* cited by examiner

*Primary Examiner* — Alton Pryor
(74) *Attorney, Agent, or Firm* — Edward K. Welch, II; IP&L Solutions

(57) ABSTRACT

Bioactive agrichemical concentrates and compositions having improved bioactivity comprising combinations of acid solutions and conventional bioactive agrichemical actives or formulations.

23 Claims, No Drawings

BIOACTIVE ACID AGRICHEMICAL COMPOSITIONS AND USE THEREOF

The present patent application is a continuation of U.S. patent application Ser. No. 12/154,135 filed May 19, 2009, now U.S. Pat. No. 8,282,949 B2 issued on Oct. 9, 2012, which claims the benefit of prior filed U.S. Provisional Patent Application No. 60/930,913, filed May 18, 2007, and entitled "Bioactive Compositions and Use Thereof" which is hereby incorporated herein in its entirety by reference.

FIELD OF THE INVENTION

The present invention relates to novel bioactive concentrates as liquid solutions or solid compositions comprising an acid and one or more sources of antimicrobial metal ions, alone or, preferably, in further combination with one or more surfactants capable of interacting with cell wall membranes of microorganisms, especially pathogenic microbes. These bioactive concentrates may be diluted with liquid or solid diluents for use in a wide variety of end-use applications, including, in particular, as bioactive agrichemicals for the control, inhibition and/or killing of micro-organisms, especially fungi, bacteria and/or plant, stramenophile and fungi-like protists.

BACKGROUND OF THE INVENTION

Bioactive materials for killing or inhibiting the growth and/or proliferation/spreading of bacteria, fungi, and other microorganisms have long been sought and employed in society. Their use dates back centuries, if not thousands of years. Early applications had ranged from pharmaceutical or health related applications to disinfectant and purification applications and more. More recent applications include a whole host of uses, with the largest use, by volume, seen in the agricultural industry. Perhaps one of the earliest bioactive materials was metallic silver and, subsequently, silver salts.

While early bioactive agents were most often metals and simple metal salts, modern science and chemical synthesis have enabled the development and production of synthetic agents, most often organic and organometallic agents, for antibacterial, antifungal and other like applications. Indeed, for many applications, especially pharmaceutical applications, the organic agents have, for the most part, eclipsed the use of inorganic bioactive agents. While inorganic and organometallic materials still command a significant market share of the agrichemical business, their use is limited due to their health and safety concerns, especially from an environment perspective. Indeed, organic bioactive agents command a huge portion of the agrochemical business.

Despite the great success and huge market share/volume commanded by organic pharmaceutical, antibacterial and agrochemical agents, they have not come without cost and consequences. In all areas of applications, a marked and growing trend has emerged: namely the manifestation and spreading of a resistance to such organic agents in most all, if not all, microorganisms. While this resistance is neither universal nor complete, it is growing and involves more and more organic agents. As their resistance grows, so too does their apparent virulence. In this respect, we are all well aware of the growing resistance of bacteria, especially pathogenic bacteria, to traditional pharmaceutical antibiotic agents and the subsequent appearance of what are commonly referred to as superbugs: pathogenic bacteria that show strong resistance to traditional organic antibacterial and pharmaceutical agents.

And, whether a direct or indirect consequence of the appearance of superbugs and/or the growing awareness of the ease by which bacteria can spread combined with an increasing concern for potentially pandemic diseases such as SARS and Bird Flu, we have become a population that is more and more pre-occupied with hygiene and general cleanliness. Consequently, there has been a huge proliferation and exponential growth in the widespread and indiscriminate use and application of cleansers and disinfectants that contain organic antimicrobial agents, all in an effort to ward off exposure to bacteria and, especially, superbugs. However, this indiscriminate use of organic agents has come with, or at least presents the possibility for, an overall increase in antimicrobial resistant organisms. By eradicating the weaker organisms, the stronger and, most often more damaging, organisms are left.

A similar consequence has manifested itself in the agricultural industry as well, especially in that portion relating to crop/food production. The widespread and repetitive use of organic biocides, fungicides, antibacterial agents and the like, has led to the manifestation of less and less efficacy of the same against the targeted diseases: an indicator of a growing resistance. Perhaps more alarming is the speed with which such resistance has begun to appear. For example, despite the great fanfare and promise behind the introduction of strobilurin fungicides in the mid-1990s, resistance had been found after just a couple years use in certain applications. Such a growing trend bodes ill for an industry where fewer and fewer acres are called upon to produce more and more crops to feed the ever growing populations while those organisms and microorganisms responsible for attacking such crops become stronger and stronger and more and more resistant to traditional control means.

While resistance is certainly of great concern, perhaps and even greater concern is the human and environmental toll associated with the widespread use of organic antimicrobial agents. For more than half a century now, more and more scientific literature has appeared correlating long-term exposure (direct and indirect) and use of such organic agrichemicals to various diseases and teratogenic, mutanogenic, and other adverse health consequences in animals and, more importantly, the human population. Perhaps the watershed of this awareness is represented by the outcry relating to the use of DDT and like pesticide agents in the 1960s. In humans, such a correlation of birth defects, cancer, and other diseases with organic agrichemicals is especially disconcerting for those whose water supplies have or may become contaminated with such organic agents due to their and/or their by-product's solubility and long half-lives. Of course drinking water is only one exposure source: another exposure source concern is inhalation from dust blown up from the fields, from wayward aerosols and/or particulates during aerial spraying and dusting, respectively, and from exposure to the clothing of workers who, themselves, were exposed in the fields or during application.

In an effort to move away form organic agents, more recent attention has once again focused on the inorganic agents, including organometallic agents, since these tend to show or have no, or certainly less, tendency to result in resistant bacteria, fungi and the like. However, such a trend merely reawakens the debates and concerns relative to the large-scale dumping of heavy metals in the environment. Although some efforts have recently focused on improving the old, traditional inorganic agents, much more effort, particularly in the non-agricultural arena, has seemingly focused on more complex species and systems, in essence, synthesized inorganic biocides such as the antimicrobial ion-exchange type antimicrobial agents based on zeolites, hydroxy apatite, and zirconium phosphates. Other recent biocides include those based on electrolytically generated silver citrates; thiol-free, specialty complexes of antimicrobial metals; sulfuric acid/sulfate complexes prepared under high pressure and temperature; and the like. While effective, these have limited applications and entail added costs owing to the complex and/or lengthy synthetic processes by which they are prepared. The latter is of especial concern in the agricultural industry where the relative cost to performance trade-off oftentimes precludes the use of functionally very viable options. Here, a few cents per acre difference, even a fraction of a cent difference per acre, can mean the world of difference in the acceptability and utility of a given agent.

Despite their inherent environmental and health concerns, the use of "natural" inorganic agents, including manufactured/processed inorganic agents, has been pushed more and more by various environmental and conservation groups, as well as health advocates, as a favorable replacement to organic agents. While such pressure alone is not likely to change the industry, the growing resistance to organic agents combined with the higher and higher costs of synthetic organic agents, is certainly having an impact: not only in the agricultural industry but across the board in all applications for such bioactive agents. However, as noted above, the reintroduction of and/or increased use of inorganic agents merely brings to the forefront the very issues that caused them to be pushed back to begin with, namely environmental toxicity and contamination and bioaccumulation. Concern is not just for the effects during application, but more so for the long term effects associated with the continual build-up of these inorganic agents or their derivatives, especially the metals, in the environment and in living organisms. Such build-up not only pertains to the soils that are treated but also underground water supplies that may be replenished from the treated fields. Concern also exists, sometimes more so, for the consequences of rain-water run-off carrying the metals into local streams and, again, downstream water supplies. Ultimately, this build-up also occurs in the food chain, with higher and higher concentrations being found in those species in the higher order of the food chain. Ultimately, this affects the human supply chain as seen, for example with mercury and other metals in tuna and swordfish. While many metals, at least at low exposure levels, have little or no affect on humans, their impact is far greater on marine and other aquatic life, especially fish, which tend to be extremely sensitive to heavy metals, like silver, resulting in increase stress and, in extreme exposure situations, widespread kills.

Consequently, as part of this resurgence of inorganic bioactive agents, there has been a significant increase in research and development dollars and time spent to address concerns relative to the use of such inorganic agents. A prime focus has been with respect to making more concentrated materials that, it is hoped, will enable the use of less overall materials. In the agrichemical arena, one of the inorganic agents receiving the greatest attention, owing to its high efficacy, is copper. Indeed, it is thought that copper could see a manifold increase in use as organic agents are either precluded from use or farmers opt out for more natural agents. According to NCFAP data, in 1997 more than 13.7 million pounds of copper was used in fungicide applications as compared to 40 million pounds of synthetic fungicides at a treatment rate of about one-half that of copper. If all synthetic fungicides were to have been supplanted by copper, it would have resulted in an increase of more than 80 million pounds of copper released into the environment. Now, ten years later, though data is not available, one can only assume the amounts are much higher. Furthermore, this is but one use of copper: copper and copper based bioactive compositions are also used in other areas such as algaecides, etc. Regardless, it is clear that any significant shift from synthetic to copper fungicides, algaecides, etc. means a huge impact and release of copper into the environment.

As noted above, recent R&D efforts with inorganic fungicides have focused on the development of improved inorganic agents that produce better effects with less application. Indeed, in August 2006, DuPont, one of the leading manufacturers of agrichemicals, especially copper based fungicides, announced certain breakthroughs, as they described them, in copper fungicides, specifically its Kocide 3000 copper hydroxide based fungicide, touting their ability to provide more antifungal action with less copper. Still, its typical application rate is on the order of 1650 grams of copper per acre per application, with somewhat lower rates, 330 grams per acre, allowed for certain applications. While certainly an improvement over conventional or traditional copper based fungicides which are applied at nearly 4.5 pounds per acre, it still means the intentional release of huge amounts of copper into the environment, even more if the environmentalists are successful in removing or banning the use of more and more organic agents.

Thus, there is still a tremendous need for cost effective, inorganic agrichemical agents that provide good antimicrobial, antifungal, antibacterial, etc., activity without concern for resistance build-up.

In following, there is a need for inorganic antimicrobial, antifungal, antibacterial, etc., agents that may be used universally, or nearly so, without concern, or certainly with reduced concern for environmental contamination and toxicity, especially less so than exists with current inorganic agents.

Similarly, there is a need for inorganic agents that are stable and easy to use, and provide good short term and, preferably, longer term efficacy as compared to many of the current short lived organic agents.

Additionally, there is a need for such inorganic agents that can safely be use in agricultural and horticultural applications, including soil and seed treatment, crop/food producing plants and trees, ornamental and flowing plants and tress, fee and ornamental grasses, and the like with minimal exposure concerns.

Furthermore, there is a need for inorganic bioactive agents that can be use in combination with conventional inorganic and, preferably, organic agrichemical actives and compositions, especially, antimicrobial, antifungal, antibacterial, anti-protist, etc. agents with synergistic results; thus, enabling less use, overall, of such actives.

Finally, there is a need for bioactive agents that provide efficacious antimicrobial, antifungal, antiprotist, and/or antibacterial performance with minimal release of inorganic metals to the environment.

SUMMARY OF THE INVENTION

According to one aspect of the present invention there are provided solid form bioactive concentrates comprising an acid, especially a weak or moderate acid, at least one source of at least one antimicrobial metal ion, and, optionally, though preferably, at least one surfactant, especially at least one anionic, non-ionic and/or amphoteric surfactant, that impacts or interacts with cell wall membranes of microorganisms, especially pathogenic microbes, or the function thereof, said acid being present in at least 40 weight percent, preferably from 40 to 80 percent, based on the total weight of the bioactive acid composition, and at a level that represents at least a 2 times molar excess relative to the antimicrobial metal ions of the source, said bioactive acid composition having a pH of less than 6, preferably from about 1.5 to 5, when diluted in a solvent, especially water, to a point where the amount of antimicrobial metal ion is 500 ppm or less in the case of a single ion or 1000 ppm or less in the case or multiple antimicrobial metal ions. These solid concentrates may be let down by dry blending with solid diluents or fillers or they may be diluted and transformed into liquid form using liquid diluents or fillers for use in various end-use applications.

According to a second aspect of the present invention there are provided liquid form bioactive concentrates comprising a concentrated aqueous or aqueous-based acid solution, especially of a weak or moderate acid, at least one antimicrobial metal ion or antimicrobial metal ion source, fully or partially dissolved in said acid solution, and, optionally, though preferably, at least one surfactant, especially at least one anionic, non-ionic and/or amphoteric surfactant, that impacts or interacts with cell wall membranes of microorganisms, especially pathogenic microbes, or the function thereof, wherein the concentration of the acid, based on the total weight to the bioactive acid solution is at least about 40 weight percent, preferably from 40 to 80 percent, acid and the acid is present a level that is at least a 2 times molar excess relative to the antimicrobial metal ion(s), and wherein, the pH of the bioactive acid solution is less than 6, preferably 1.5 to 5, when the concentrated bioactive acid solution is diluted in a solvent, especially water, to a point where the amount of antimicrobial metal ion is 500 ppm or less in the case of a single ion or 1000 ppm or less in the case or multiple antimicrobial metal ions. These liquid concentrates may be let down by mixing with an appropriate solvent, most especially water or an aqueous-based solvent, for application. Alternatively, especially for agricultural, including horticultural, applications, the concentrate may be applied as is or in a diluted state to a solid, absorbent material for ultimate end-use application.

According to a third embodiment of the present invention, there are provided flowable bioactive agrichemical compositions in particle form, e.g., dusts, granules, powders, or combinations thereof, comprising a solid carrier particle which has been treated with a bioactive acid solution, especially an aqueous or aqueous-based solution, having a pH of less than 6, preferably 1.5 to 5, and comprising an acid, especially a weak or moderate acid, at least one antimicrobial metal ion source, and, optionally, though preferably, at least one surfactant, especially at least one anionic, non-ionic and/or amphoteric surfactant, that impacts or interacts with cell wall membranes of microorganisms, especially pathogenic microbes, or the function thereof, said acid present in a molar excess, relative to the antimicrobial metal ions, where the amount of antimicrobial metal ion is 500 ppm or less in the case of a single ion or 1000 ppm or less in the case or multiple antimicrobial metal ions.

According to a fourth embodiment of the present invention, there are provided flowable bioactive agrichemical compositions in particle form, e.g., dusts, granules, powders, or combinations thereof, comprising a bioactive acid composition in particle form, preferably a powder, said bioactive agrichemical composition having been made by i) forming an aqueous solution of an acid, especially a weak or moderate acid, at least one antimicrobial metal ion source, and, optionally, though preferably, at least one surfactant, especially at least one anionic, non-ionic and/or amphoteric surfactant, that impacts or interacts with cell wall membranes of microorganisms, especially pathogenic microbes, or the function thereof, said acid present in a molar excess, relative to the antimicrobial metal ions, where the amount of antimicrobial metal ion is 500 ppm or less in the case of a single ion or 1000 ppm or less in the case or multiple antimicrobial metal ions, ii) allowing the water to evaporate to form the solid bioactive acid and iii) if necessary, grinding or crushing the formed solid bioactive acid to form a powder.

According to a fifth embodiment of the present invention there are provided liquid bioactive agrichemical compositions comprising a) a suitable solvent or solvent system, b) an acid, especially a weak or moderate acid, e) at least one antimicrobial metal ion source, and d) optionally, though preferably, at least one surfactant, especially at least one anionic, non-ionic and/or amphoteric surfactant, that impacts or interacts with cell wall membranes of microorganisms, especially pathogenic microbes, or the function thereof, wherein the solution of the acid and solvent has a pH of less than 6, preferably 1.5 to 5, prior to, and preferably after as well, the addition of the conventional bioactive agrichemical active, said acid (b) is present in a molar excess relative to the antimicrobial metal ions of the source (c) and wherein the amount of antimicrobial metal ions attributed to the source (c) is 500 ppm or less in the case of a single ion or 1000 ppm or less in the case or multiple antimicrobial metal ions. Most preferably, the solvent is water or a water-based solvent system, most preferably water, and the acid and the antimicrobial metal ion source are all wholly or substantially soluble or miscible in the solvent. Where desired, it is also possible to add the solution to a second, non-aqueous solvent, including a lipophilic solvent, to form a suspension or emulsion.

According to a sixth embodiment of the present invention there is provided a method of making a solid form bioactive agrichemical concentrate comprising dry mixing a) an acid, especially a weak or moderate acid, b) at least one source of at least one antimicrobial metal ion, and c) optionally, though preferably, at least one surfactant, especially at least one anionic, non-ionic and/or amphoteric surfactant, that impacts or interacts with cell wall membranes of microorganisms, especially pathogenic microbes, or the function thereof, said acid being present in at least 40 weight percent, based on the total weight of the acid and antimicrobial metal ions source, and at a level that represents at least a 2 times molar excess relative to the antimicrobial metal ions of the source, the acid being present in an amount whereby a solution made by adding the acid and the antimicrobial metal ions source to water will have a pH of less than 6, preferably from about 1.5 to 5, when diluted to a point where the amount of antimicrobial metal ion is 500 ppm or less in the case of a single ion or 1000 ppm or less in the case or multiple antimicrobial metal ions.

According to a seventh embodiment of the present invention there is provided a method of making a solid form bioactive concentrate comprising i) dissolving a) an acid, especially a weak or moderate acid, b) at least one source of at least one antimicrobial metal ion, and c) optionally, though preferably, at least one surfactant, especially at least one anionic, non-ionic and/or amphoteric surfactant, that impacts or interacts with cell wall membranes of microorganisms, especially pathogenic microbes, or the function thereof, in a volatile solvent, especially water or a water-based solvent, ii) allowing the solvent to evaporate to leave a solid cake, granules, or powder, and iii) if necessary or desired, grinding the cake to form granules or a powder, wherein the acid is present in at least 40 weight percent, based on the total weight of the acid and antimicrobial metal ions source, and at a level that represents at least a 2 times molar excess relative to the antimicrobial metal ions of the source, the acid being present in an amount whereby a solution made by adding the acid and the antimicrobial metal ions source to water will have a pH of less than 6, preferably from about 1.5 to 5, when diluted to a point where the amount of antimicrobial metal ion is 500 ppm or less in the case of a single ion or 1000 ppm or less in the case or multiple antimicrobial metal ions.

According to an eighth embodiment of the present invention there is provided a method of making a liquid bioactive agrichemical concentrate said method comprising forming a concentrated aqueous or aqueous-based acid solution of an acid, preferably a weak or medium acid, wherein the concentration of the acid is at least 40% by weight, dissolving in the concentrated acid solution at least one antimicrobial metal ion source and, optionally, though preferably, at least one water-soluble surfactant, preferably an anionic, non-ionic and/or amphoteric surfactant.

According to a ninth embodiment of the present invention there is provided a method of preventing or inhibiting the growth of plant pathogens, especially fungi, bacteria and/or plant, stramenophile and fungi-like protists in agricultural, including horticultural, applications, said method comprising applying to the seeds of the pertinent crop or plant; to the soil in which the seed, crop or plant is or is to be planted; to the aqueous environment in which the plants are growing; or to the matter of the plant itself, a flowable bioactive agrichemical composition in particle form comprising a solid carrier particle which has been treated with a bioactive acid solution, especially an aqueous or aqueous-based solution, having a pH of less than 6, preferably 1.5 to 5, and comprising an acid, especially a weak or moderate acid, at least one antimicrobial metal ion source, and, optionally, though preferably, at least one surfactant, especially at least one anionic, non-ionic and/or amphoteric surfactant, that impacts or interacts with cell wall membranes of microorganisms, especially pathogenic microbes, or the function thereof, said acid present in a molar excess, relative to the antimicrobial metal ions, where the amount of antimicrobial metal ion is 500 ppm or less in the case of a single ion or 1000 ppm or less in the case or multiple antimicrobial metal ions. Most preferably, the composition according to this method will further comprise at least one agent for adhering or enhancing the adherence of the bioactive agrichemical actives to the matter being treated. Generally speaking, the inventive bioactive agrichemical composition will be applied at a rate or amount whereby the amount of the bioactive acid solution originated antimicrobial metal ion(s) applied will be no more than about 500 grams per acre, preferably no more than 250 grams per acre.

According to a tenth embodiment of the present invention there is provided a method of preventing or inhibiting the growth of plant pathogens, especially fungi, bacteria and/or plant, stramenophile and fungi-like protists in agricultural, including horticultural, applications, said method comprising applying to the seeds of the pertinent crop or plant; to the soil in which the seed, crop or plant is or is to be planted; to the aqueous environment in which the plants are growing; or to the matter of the plant itself, a flowable bioactive agrichemical composition in particle form said bioactive agrichemical composition having been made by: i) forming an aqueous solution of an acid, especially a weak or moderate acid, at least one antimicrobial metal ion source, and, optionally, though preferably, at least one surfactant, especially at least one anionic, non-ionic and/or amphoteric surfactant, that impacts or interacts with cell wall membranes of microorganisms, especially pathogenic microbes, or the function thereof, said acid present in a molar excess, relative to the antimicrobial metal ions, where the amount of antimicrobial metal ion is 500 ppm or less in the case of a single ion or 1000 ppm or less in the case or multiple antimicrobial metal ions, ii) allowing the water to evaporate to form the solid bioactive acid and iii) if necessary, grinding or crushing the formed solid bioactive acid to form a powder. Most preferably, the composition according to this method will further comprise at least one agent for adhering or enhancing the adherence of the bioactive agrichemical actives to the matter being treated. As with the previous embodiment, the formulation of the inventive bioactive agrichemical composition will be such that the antimicrobial metal ion(s) applied will be no more than about 500 grams per acre, preferably no more than 250 grams per acre.

According to an eleventh embodiment of the present invention there is provided a method of preventing or inhibiting the growth of plant pathogens, especially fungi, bacteria and/or plant, stramenophile and fungi-like protists in agricultural, including horticultural, applications, said method comprising applying to the seeds of the pertinent crop or plant; to the soil in which the seed, crop or plant is or is to be planted; to the aqueous environment in which the plants are growing: or to the matter of the plant itself, liquid bioactive agrichemical compositions comprising a) a suitable solvent or solvent system, b) an acid, especially a weak or moderate acid, c) at least one antimicrobial metal ion source, and d) optionally, though preferably, at least one surfactant, especially at least one anionic, non-ionic and/or amphoteric surfactant, that impacts or interacts with cell wall membranes of microorganisms, especially pathogenic microbes, or the function thereof, wherein the solution of the acid and solvent has a pH of less than 6, preferably 1.5 to 5, prior to, acid present in a molar excess relative to the antimicrobial metal ions of the source (c) and wherein the amount of antimicrobial metal ions attributed to the source (c) is 500 ppm or less in the case of a single ion or 1000 ppm or less in the case or multiple antimicrobial metal ions. Most preferably, the solvent is water or a water-based solvent system, most preferably water, and the acid and the antimicrobial metal ion source are all wholly or substantially soluble or miscible in the solvent. Generally speaking, this formulation of the inventive bioactive agrichemical composition will be such that, when applied in use, the application rate or amount of the bioactive acid solution originated antimicrobial metal ion(s) applied will be no more than about 500 grams per acre, preferably no more than 250 grams per acre.

In as much as a key objective of the present invention is to lessen the amount of metals entering the environment, preferred embodiments of each of the foregoing embodiments will such that the contribution of antimicrobial metal ions from the antimicrobial metal ion source will be no more than 300 ppm, most preferably no more than 50 ppm, in the case of a single antimicrobial metal ion and no more than 500 ppm, preferably no more than 150 ppm, in the case of multiple antimicrobial metal ions.

In as much as it is also an objective of the present invention to avoid the use of materials that induce phytotoxicity, the acids are preferably organic acids, most preferably carboxylic acids, and/or the bioactive acid solution, in the diluted state has a pH of greater than 2 and less than 6.

DETAILED DESCRIPTION

The present invention embraces many different embodiments, as set forth above, all of which have significant degree of common characteristics and make-up. Yet, while the foregoing sets forth each embodiment in its most general respect, there are many aspects of each that are, in certain embodiments, common and others that are unique to their embodiments. In its most fundamental respect, the invention pertains to bioactive concentrates comprising a) one or more antimicrobial metal ions or ion sources, b) an acid or in an acidic solution, and c) optionally, though preferably, one or more surfactants for combating or preventing the growth or proliferation of fungi, bacteria, viruses, and plant, stramenophile and fungi-like protists, as well as bioactive agrichemical products and formulated based on diluted forms of the foregoing. These concentrates and agrichemical products may exist in solid or liquid form and may include any number of additives typical for their intended end-use application. As bioactive agrichemical materials and products, these compositions are especially useful, and most often synergistically, when combined with or made to include a conventional agrichemical active or formulated active. The latter compositions are more fully discussed in and the subject of International Patent Application Publication No. WO 2008/144015 and United States Published Patent Application Nos. US 2008/0292673 A1, US 2008/0292674 A1, and US 2008/0299222 A1, all of which are entitled "Bioactive Agrichemical Compositions and Use Thereof" and were filed on the same day as this application with the same inventors as the present application, all of which are incorporated herein in their entirety by reference.

For convenience in drafting and simplicity in reading this application, the word "bioactive" is intended to include agents that kill or prevent or inhibit the growth and/or proliferation of bacteria, fungi, viruses, and plant, stramenophile and fungi-like protests, particularly those that affect or adversely affect, even from a purely esthetic standpoint, plants and trees, especially those associated with the agricultural and horticultural products including food crops, feed crops, flowers, ornamentals, turf, and the like, i.e., plant pathogens. Oftentimes, the present invention is discussed in terms of "fungicides" and "antifungal activity" as well as fungicidal actives; though it is to be understood that it is not limited thereto.

Similarly, the word "active" refers to those compounds or compositions that are directly responsible for the bioefficacy of the bioactive agrichemical in addressing or attacking the target organism. A formulated active is one that in addition to the active ingredient also contains one or more other constituents that may or may not influence the bioefficacy of the active, but in any event are not themselves directly responsible for killing or preventing the growth of the targeted microorganism. Further, as a matter of clarification, the terms "bioactive acid composition" and "bioactive acid solution" are oftentimes used herein and relate to the solid and liquid forms, respectively, of the concentrates and diluted forms of the compositions of the present invention, or both are referred to as the "bioactive acid solution or composition."

The acids that may be used in the present invention are either solid or liquid in their natural state, but are readily dissolved in or miscible with water or an aqueous based solvent or the organic carrier or diluent employed for the particular application to be addressed. For example, if one is intending to make an oil or oil-based (or other non-aqueous solvent based) fungicide, e.g., for use in an aqueous environment, either the components of the bioactive composition must be soluble in or miscible with the chosen oil or other non-aqueous or lipophilic solvent or the aqueous or aqueous-based bioactive acid solution is to be combined with the oil or other non-aqueous or lipophilic solvent to form an emulsion or suspension.

Exemplary acids include the organic acids, especially the carboxylic acids such as citric acid, valeric acid, itaconic acid, acetic, citriconic acid, lactic acid, marc acid, succinic acid, aldaric acid, malonic acid, proprionic acid, malonic acid, maleic acid, salicylic acid, glutaric acid, tartaric acids, benzoic acid and the like, as well as the mineral acids such as nitric acid, sulfuric acid, phosphoric acid, boric acid, and the like. The preference is for weaker or moderate acids such as aldaric, citric, malic, and lactic acids as opposed to the moderate to strong mineral acids like boric and phosphoric acids. However, strong acids, especially strong mineral acids like sulfuric or nitric acid, may be used; however, depending upon the strength of the acid, it may be preferable to buffer the acid so as to avoid handling and use problems, especially problems associated with the substrate to which the bioactive composition is to be applied. This is particularly important for bioactive agrichemical compositions to be applied to plants, animals and crops or foodstuffs since the acid may damage the substrate, directly or indirectly. In plants, for example, there is considerable concern for phytotoxicity resulting from acid treatments alone or in combination with metal compounds such as copper fungicides and the like. Thus, while efficacious, it is most preferable to avoid mineral acids and, instead, employ carboxylic acids. Additionally, though some suitable acids fall outside of this range, it is desirable that the pica (in water @ 25° C.) of the acid be greater than 0, preferably greater than 1, most preferably greater than 1.5.

Generally speaking, and despite the strong efficacy of phosphoric acid and nitric acid, it is preferred that weak or moderate acids be used. This is especially desirable as it avoids the potential need for buffering agents, which are not desired. While it is to be appreciated that other surfactants, fungicides, wetting agents, emulsifiers, and the like that may be, and, depending upon the end use application, are likely to be added to the inventive compositions of the present invention, may have a buffering effect on the pH of these bioactive systems, this effect is not an intended or necessarily desirable effect. Indeed, it may be necessary to add more acid to the composition in order to maintain the required level of acidity.

As noted, acidity is critical to the efficacy of the bioactive concentrates and compositions, especially agrichemical compositions, of the present invention. Generally speaking, the pH of the bioactive acid solution or bioactive acid composition prepared using purified water will be less than 6, preferably from about 1.5 to 5 and more preferably from about 2 to about 4, most preferably greater than 2. Most preferably, the fully formulated end-use products, especially the bioactive agrichemical compositions, of the present invention will also meet the foregoing pH limitations when prepared or when diluted with purified water to that concentration that is to be applied. In the case of assessing or confirming the pH of the solid bioactive composition or a solid bioactive agrichemical composition according to the present invention, the bioactive composition or, as appropriate, the bioactive agrichemical is first dissolved in purified water to a concentration equivalent to that at which it would be applied in use, and the pH measured. As acknowledged in the technical art generally, purified water has a neutral pH, ~pH 7.

The second critical aspect of the acid concentration relates to the molar equivalence to the antimicrobial metal ions present in the bioactive acid composition or bioactive acid solution. At a minimum, there must be a 2 times molar excess, though preferably there is at least a 5 times, and most preferably at least a 10 times, molar excess acid. These levels are typically attained by formulating bioactive acid solutions whereby the acid concentration in the final diluted state of the bioactive composition is from about 0.01% to about 10%, preferably from about 0.1% to about 4% by weight of the solution. Higher concentrations may also be used, e.g., up to 20% or more, provided that the substrate to which the bioactive composition is to be applied is not affected by the higher acid content and/or the acid is a weak or weakly moderate acid. Certainly, higher concentrations will be used in the production of concentrates as discussed below.

The second critical component of the bioactive compositions is the antimicrobial metal ion: more aptly its metal ion source. Suitable metal ions are selected from the group consisting antimicrobial transition metal ions and poor ions that have shown antimicrobial bioefficacy. Preferred metal ions are selected from the group consisting of silver, copper, zinc, mercury, tin, gold, lead, iron, bismuth, cadmium, chromium and thallium ions or combinations of any two or more of the foregoing. Most preferably, the metal ions are selected from the group consisting of silver, copper and zinc ions and combinations of any two or all three. Bioactive compositions in which at least two and preferably all three of these preferred ions are present are especially beneficial and preferred. Where multiple antimicrobial metal ions are present, each will be present in a molar amount of 3 to 97 percent, preferably 9 to 91 percent, more preferably 20 to 80 percent. In its preferred embodiment, where multiple metal ions are present, they will be present in an equal amount whereby no one metal ion is more than 20 times, more preferably no more than 10 times that of any other metal ion. Especially good results have been found where each antimicrobial metal ion is present in an equal amount, by weight.

The metal ion is added to the acid solution or, as appropriate, the acid, in the form of a source compound, salt or complex that readily releases the ions or otherwise dissociates in the acid solution or when the source and acid are dissolved in a solvent, especially water or a water-based solvent. Exemplary salts and organometallic compounds that may suitably serve as the ion sources include the respective oxides, sulfides, carbonates, nitrates, phosphates, dihydrogen phosphates, sulfates, oxalates, quinolinolates, thiosulfates, sulfonates, phthalates, hydroxides, glycolates, and the like of the antimicrobial metals as well as the carboxylic acid salts thereof, especially the simple carboxylates, such as the citrates, benzoates, acetates, lactates, etc. of said antimicrobial metals. Other salts such as the halide salts and substituted halide salts, such as the halides, hexafluoroantimonates, tetrafluoroborates, and perchlorates of said antimicrobial metals may be used though they are less desirable as they tend to have slow and/or poor solubility, especially in water. Specific metal ion sources include, but are certainly not limited to, silver nitrate, silver oxide, silver acetate, silver citrate, cupric oxide, copper hydroxide, cuprous oxide, copper oxychloride, cupric acetate, copper quinolinolate, copper citrate, zinc oxide, zinc citrate, and the like.

It has also been surprisingly found that certain inorganic complexes may also serve as the metal ion source. Specifically, ion-exchange type antimicrobial agents and dissolving glass antimicrobial agents may be used where the carrier matrix of these materials is soluble in the acid or diluted acid. For example, it has been found that zeolites are readily soluble in concentrated citric acid. Here the metal ion source or sources are added to the acid with mixing until the particles are dissolved. It is also contemplated that these metal ion sources may be only partially dissolved so as to provide for a longer term source of the antimicrobial metal ion. While these ion sources tend to dissolve in the diluted acid, to speed up and/or enhance the dissolving of the metal ion source, it is preferable to dissolve them in a concentrated acid solution, preferably one of from about 40% to 80% concentration.

Suitable ion-exchange type agents include, but are not limited to aluminosilicates, zeolites, hydroxyapatite, and zirconium phosphates, all of which are commercially available and/or fully described in the patent literature. For example, antimicrobial metal ion-containing hydroxyapatite particles are described in, e.g., U.S. Pat. Nos. 5,009,898 and 5,268,174; antimicrobial metal ion-containing zirconium phosphates are described in, e.g., U.S. Pat. Nos. 4,025,608; 4,059,679; 5,296,238; 5,441,717 and 5,405,644 as well as in the Journal of Antibacterial and Antifungal Agents, Vol. 22, No. 10, pp. 595-601, 1994; and antimicrobial metal ion-containing aluminosilicates and zeolites are described in, e.g., U.S. Pat. Nos. 4,911,898; 4,911,899; 4,938,955; 4,938,958; 4,906,464; and 4,775,585, all of the aforementioned patents hereby being incorporated herein by reference in their entirety. Suitable soluble glasses include those described in, e.g., U.S. Pat. No. 5,470,585, which is also incorporated herein by reference in its entirety.

While individual metal ion sources may be used, it is also desirable to use combinations of metal ion sources so as to provide a mixture of metal ions. In certain instances, a single source may provide multiple metal ions. For example, preferred ion-exchange type metal ion sources include AgION AJ10D which contains both silver and zinc ions and AgION AC100 which includes both silver and copper ions. Most preferably, the metal ion sources are the readily soluble salts and compounds, as mentioned above, and most preferably the combination of such compounds whereby solutions having equal or relatively equal concentrations of each of silver, copper and zinc ions are prepared. Suitable combinations include combinations of silver citrate, copper citrate and zinc citrate as well as combinations of silver nitrate, copper sulfate and zinc oxide.

The amount of the antimicrobial metal ion source to be incorporated into the acid solution or, as appropriate, to be combined with the acid is that which is sufficient to provide a concentration of from about 1 ppm to about 500 ppm, preferably from about 1 ppm to about 300 ppm, more preferably about 2 ppm to about 100 ppm, most preferably from about 5 to about 50 ppm of each antimicrobial metal ion, in the bioactive acid solution or bioactive acid composition at its diluted, end-use concentration. Where multiple metal ions and/or metal ion sources are used to provide combinations of metal ions, the total concentration of metal ions in the solutions should be from about 2 ppm to about 1000 ppm, preferably from about 2 ppm to about 500 ppm, more preferably from about 5 ppm to 300 ppm, most preferably from about 5 ppm to about 150 ppm, in the bioactive acid solution or bioactive acid composition at its diluted, end-use concentration. Of course higher levels could be used but are not necessary to provide suitable bioefficacy and, more importantly, such higher use conflicts with the desired intent of minimizing metal addition to the environment. Thus, in following with said objective, it is preferable to use the minimal, or nearly so, amount possible for the desired application.

In agricultural and horticultural applications, phytotoxicity is especially of concern. Thus, in accordance with the agricultural and horticultural applications of this invention, especially for application to seedlings and plants, the level of the metals should be less than would otherwise cause phytotoxicity. Most preferably, as noted above, the objective is to use as low a level of metal ion as is reasonably possible yet continue to provide the benefits desired, especially fungicidal, protisticidal, and/or antimicrobial properties. This concern is especially pertinent to those compositions containing copper alone or in combination with one or more of the other antimicrobial metal ions and most especially, where the bioactive acid solution or composition is to contain or be used in conjunction with another copper or copper-based material. In this respect, it should be noted that the aforementioned limitations on the antimicrobial metal ions refers only to those antimicrobial metal ions contributed by the one or more sources of antimicrobial metal ions associated with the bioactive acid solution or bioactive acid composition, and not to the copper or any other antimicrobial metals or metal ions that may be contributed by other compounds or materials to be used in conjunction or in combination with the bioactive acid solutions or bioactive acid compositions.

Optionally, though preferably, the bioactive acid solutions or bioactive acid compositions, and, in any event, the bioactive agrichemical compositions of the present invention include one or more surfactants, especially water soluble surfactants. Although good results have been achieved in weak and moderate acid bioactive acid solutions without the surfactants, the use of the surfactant should be and is generally preferred with such acids. Furthermore, while certain strong and very strong acids, especially mineral acids, do not warrant the need for surfactants, e.g., phosphoric acid, it is especially desirable, and in some instances necessary, e.g., where other than only short term bioefficacy is desired, to employ one or more surfactants. Especially preferred surfactants are those that affect or interact with cell walls or membranes of microorganisms, especially pathogenic microbes, or their function. Suitable surfactants include anionic, cationic, non-ionic and amphoteric (e.g., zwitterionic) surfactants, especially those that are water soluble or show relatively good water solubility. Preferably the surfactants are anionic, non-ionic and/or amphoteric surfactants such as the sulfonates, sulfates, sulfosuccinates, sarcosinates, mono and diglycerides, amine oxides, ether carboxylates, betaines, sulfobetaines, gylcinates and the like. Generally, cationic and those non-ionic surfactants having polyalkylether units, especially polyethylene oxide units, with degrees of polymerization of the alkylene ether unit of greater than about 6 do not show the same level of effedives in providing synergy to the bioactive compositions as the other surfactants. Nonetheless, such surfactants may be used in combination with effective surfactants so long as they do not materially detract from or reduce the bioefficacy of the compositions.

The surfactant is typically used in conventional amounts, i.e., will be added to the bioactive acid solutions or bioactive acid compositions in an amount whereby the concentration of the surfactant in the end-use diluted state of the bioactive agrichemical compositions is consistent their use level in traditional fungicides. Generally speaking, the surfactant will be present in an amount of from about 0.001% to about 3%, preferably from about 0.01% to about 0.5%, by weight based on the total weight of the bioactive acid solution or bioactive acid composition in the diluted state. While higher loadings could be used, it is not necessary to manifest the desired synergy in bioefficacy. Generally, where the surfactant is basic in nature or one that hydrolyzes in water to form a basic solution, the amount should be minimized and/or the amount of acid increased so as to avoid too much neutralization of the bioactive acid solution.

Exemplary anionic surfactants and classes of anionic surfactants suitable for use in the practice of the present invention include: alcohol sulfates; alcohol ether sulfates; alkylaryl ether sulfates; alkylaryl sulfonates such as alkylbenzene sulfonates and alkylnaphthalene sultanates and salts thereof; alkyl sultanates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sultanate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coca hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated tridecylalcohol phosphate ester; dialkyl sulfosuccinates; perfluoro ($C_6$-$C_{18}$)alkyl phosphonic acids; perfluoro($C_6$-$C_{18}$)alkyl-phosphinic acids; perfluoro($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides.

Exemplary amphoteric and cationic surfactants include alkylpolyglycosides; betaines; sulfobetaines; glycinates; alkanol amides of $C_8$ to $C_{18}$ fatty acids and $C_8$ to $C_{18}$ fatty amine polyalkoxylates; $C_{10}$ to $C_{16}$ alkyldimethylbenzylammonium chlorides; coconut alkyldimethylaminoacetic adds; phosphate esters of $C_8$ to $C_{18}$ fatty amine polyalkoxylates; alkylpolyglycosides (APG) obtainable from a acid-catalyzed Fischer reaction of starch or glucose syrups with fatty alcohols, in particular $C_8$ to $C_{18}$ alcohols, especially the $C_8$ to $C_{10}$ and $C_{12}$ to $C_{14}$ alkylpolyglycosides having a degree of polymerization of 1.3 to 1.6, in particular 1.4 or 1.5.

Exemplary non-ionic surfactants and classes of non-ionic surfactants include: polyaryiphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic dials; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereo; ethoxylated tristyrylphenol; ethoxylated fatty alcohol; ethoxylated lauryl alcohol; ethoxylated castor oil; and ethoxylated nonylphenol; alkoxylated alcohols, amines or acids, mixtures thereof as well mixtures thereof with diluents and solid carriers, in particular clathrates thereof with urea. The alkoxylated alcohols, amines or acids are preferably based on alkoxy units having 2 carbon atoms, thus being a mixed ethoxylate, or 2 and 3 carbon atoms, thus being a mixed ethoxylate/propoxylated, and having at least 5 alkoxy moieties, suitably from 5 to 25 alkoxy moieties, preferably 5 to 20, in particular 5 to 15, in the alkoxy chain. The aliphatic moieties of the amine or acid alkoxylated may be straight chained or branched of 9 to 24, preferably 12 to 20, carbon atoms. The alcohol moiety of the alcohol alkoxylates is as a rule derived from a $C_9$-$C_{18}$ aliphatic alcohol, which may be non-branched or branched, especially monobranched. Preferred alcohols are typically 50% by weight straight-chained and 50% by weight branched alcohols.

As noted above, the aforementioned surfactants may be used alone or in combination. Furthermore, while not all of the surfactants mentioned above will provide the desired synergy when used alone with the metals and acids, depending upon the ultimate end-use application for the bioactive agrichemical compositions of the present invention, they may nevertheless be used in combination with the synergistic surfactants for their intended function. For example, certain of the aforementioned surfactants may enhance the dispersion of the actives in the solvent or may enhance the wetting out of the substrate to which the inventive bioactive compositions of the present invention are applied, e.g., plants, seeds, and soil in the case of agrichemical compositions and countertops, touch surfaces, etc. in the case of disinfectants. All of these surfactant materials are well known and commercially available. Furthermore, those skilled in the art, without undue experimentation, will readily appreciate which surfactants and/or combinations of surfactants, in addition to the synergist surfactants, may be used for the specific end-use application. Again, it is important that when additional surfactants are employed for other purposes they not interfere with or have minimal interference with the synergy that results from the desired surfactants, i.e., those that show synergy in providing antimicrobial, including antibacterial and/or antifungal, activity when used in combination with the acid and metal ions.

If any interference exists and the other surfactant is necessary or otherwise desired for the application, then its use should be minimized to produce the least adverse impact on the synergy and/or attributes of the active components of the inventive bioactive agrichemicals of the present invention while manifesting the desired property for which it is to be employed. Furthermore, if there is concern with such interference, especially if the surfactants are used or to be used in an amount that will neutralize the acid of the bioactive compositions so as to render them outside of the claimed range, then those surfactants may still be added but not until the time of application. In essence the bioactive compositions of the present inventions may be employed as two- or more part systems to be mixed when applied or when preparing the diluted compositions, which are then to be immediately applied. Most preferably, it is best to avoid the use of such surfactants or those amounts of said surfactants that will adversely affect the bioefficacy of the claimed compositions.

As noted above, the bioactive compositions of the present invention may be used in conjunction or in combination with one or more other conventional bioactive agrichemical actives or formulations suitable for the intended end-use. Furthermore, as also noted above and in the aforementioned co-pending, co-filed pending International and United States patent applications, the combined use of the claimed bioactive acid solution or composition with other conventional bioactive agrichemical actives and formulations, particularly fungicides, oftentimes results in enhanced bioefficacy, a synergy that is otherwise unexpected. For example, previously non-efficacious levels of conventional bioactive actives are rendered efficacious as a result of the presence of the bioactive acid solution or composition. Similarly, these combinations oftentimes enable one to achieve the same level of bioefficacy with less than conventional application rates or amounts of the conventional bioactive agrichemical active. Additionally, and of particular significance, the combination is also believed to reduce the incidence of and/or the speed with which bio-resistance to conventional agrichemicals, especially the synthetic organic agrichemicals, is manifested in target organisms. Thus, the commercial life expectancy of these and future conventional agrichemical actives is likely to be increased and the generation of superbugs or resistant strains of the bacterial fungi, protists and the like decreased or delayed.

The bioactive agrichemical compositions according to the present invention can be used alone or, preferably and advantageously, they are used in combination with (typically as a mixture) one or more other compatible components or additives typical of agrichemical treatments and compositions including, for example, solid or liquid fillers or diluents, adjuvants, surfactants or equivalents, which are suitable for the desired use and which are acceptable for use, from an environmental, health and safety as well as regulatory perspective, in the particular intended end-use application. This is especially so for those applications where the bioactive compositions are to be used in agriculture: whether as a soil, seed, or plant treatment or in the treatment of foodstuffs, prior to or following harvest. In following, the formulations can also contain ingredients of other types, such as protective colloids, adjuvants, binders, rain fasteners, thickeners, thixotropic agents, penetrating agents, oils for spraying, stabilizers, antifreeze agents, defoaming agents, foaming agents, corrosion inhibitors, dyes, or the like, as well as other known active ingredients which have pesticidal properties (in particular fungicidal, insecticidal, acaricidal or nematicidal properties) or, in the case of in-field agricultural applications, which have plant-growth-regulating properties.

The nature and amount of the additives to be employed in the bioactive agrichemical compositions of the present invention depends, in part, upon the end-use application and the form in which the composition is to take. Specifically, the bioactive compositions of the present invention may be in the form of and/or manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. The specific procedure typically includes intensive mixing and/or milling of the bioactive compositions with the other substances. The form of application such as spraying, atomizing, dispersing, dusting, pouring and the like may be chosen based on the compositions to be applied, the desired objectives, and the given circumstances.

Although the typical definition of "filler" is a material added for the primary purpose of adding bulk, in the present application, "fillers" typically have function and utility and generally refer to organic or inorganic, natural or synthetic components with which the active components are combined to facilitate their application, for example, onto plants, seeds or the soil, for example as a carrier. These fillers are generally inert and must be acceptable for the intended application, especially for agronomic uses, in particular for treating plants.

The filler can be solid, for example clays, natural or synthetic silicates, silica, resins, waxes, solid fertilizers (for example ammonium salts), natural soil minerals, such as kaolins, clays, talc, lime, calcium carbonate, quartz, attapulgite, montmorillonite, bentonite or diatomaceous earths, or synthetic minerals, such as silica, alumina or silicates, in particular aluminium or magnesium silicates. The solid fillers which are suitable for granules are as follows: natural, crushed or broken rocks, such as calcites, marble, pumice, sepiolite or dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or dyes which, when they are solid, can also act as diluents. Where the additives are alkaline and will likely increase the pH of the compositions, e.g., talc, lime, calcium carbonate, and marble, the amount by which they are added should not cause the pH to exceed the claimed ranges or additional acid should be added to maintain the desired pH. Preferably, such materials should be avoided altogether.

The fillers can also be liquids, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethylacetamide or N-methylpyrrolidone; N-actylpyrrolidone, liquefied gases; or the like, whether they are taken separately or as a mixture.

As mentioned above, depending upon the end-use application, the inventive bioactive agrichemical compositions or formulations will contain one or more additional surfactants (additional to the surfactant(s) that are optionally part of the bioactive acid solution or bioactive acid composition) as emulsifiers, dispersing agents, wetting agents and the like. These additional surfactants may be cationic, anionic, nonionic or amphoteric surfactants or mixtures of these surfactants. Among those surfactants which are used, for example, are polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkyiphenols or aryiphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the foregoing compounds as well as those surfactants described above relative to the synergistic surfactant for the bioactive composition. Here, however, the surfactants are generally present at much higher concentrations versus that needed to show synergy with respect to the acid/metal combination. The presence of at least one additional surfactant is generally essential when the active materials and/or the inert filler are insoluble or only sparingly soluble in water and when the filler for the said composition to be applied is water. For foliar applications, the choice of surfactants is oftentimes paramount for obtaining good bioavailability of the active material(s); thus, a combination of a surfactant of hydrophilic nature (HLB>10) and a surfactant of lipophilic nature (HLB<5) will preferably be used.

In agricultural applications as well as in applications where it is desired to affix the bioactive composition to a surface, the compositions will typically have a binder, rain fastener, or other adhesive type components. Suitable binders are well known and include, e.g., water-soluble and water-dispersible film-forming polymers. Suitable polymers have an average molecular weight of at least about 1,000 up to about 100,000; more specifically at least about 5,000, up to about 100,000. The aqueous compositions generally contain from about 0.5% to about 10%, preferable from about 1.0% to about 5%, by weight of the composition of the binder, film-forming polymer and the like. Suitable film-forming polymers include, but are not limited to a) alkyleneoxide random and block copolymers such as ethylene oxide-propylene oxide block copolymers (EO/PO block copolymers) including both EO-PO-EO and PO-EO-PO block copolymers; ethylene oxide-butylene oxide random and block copolymers, $C_2$-$C_6$ alkyl adducts of ethylene oxide-propylene oxide random and block copolymers, $C_2$-$C_6$ alkyl adducts of ethylene oxide-butylene oxide random and block copolymers; b) polyoxyethylene-polyoxypropylene monoalkylethers such as methyl ether, ethyl ether, propyl ether, butyl ether or mixtures thereof; c) vinylacetate/-vinylpyrrolidone copolymers, d) alkylated vinylpyrrolidone copolymers, e) polyvinylpyrrolidone, and f) polyalkyleneglycol including the polypropylene glycols and polyethylene glycols. Specific examples of suitable polymers include Pluronic P103 (BASF) (EO-PO-EO block copolymer), Pluronic P65 (BASF) (EO-PO-EO block copolymer), Pluronic P108 (BASF) (EO-PO-EO block copolymer), Vinamul 18160 (National Starch) (polyvinylacetate), Agrimer 30 (ISP) (polyvinylpyrrolidone), Agrimer VA7w (ISP) (vinyl acetate/vinylpyrrolidone copolymer), Agrimer AL 10 (ISP) (alkylated vinylpyrrolidone copolymer), PEG 400 (Uniqema) (polyethylene glycol), Pluronic R 25R2 (BASF) (PO-EO-PO block copolymer), Pluronic R 31 R1 (BASF) (PO-EO-PO block copolymer) and Witconol NS 500LQ (Witco) (butanol PO-EO copolymer).

Additional adhesive and adhesive type materials that may be used include carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations.

It may also be desirable to thicken the bioactive compositions and formulations, especially where there is concern that the composition will quickly run off or run down the substrate to which it is applied. Suitable thickeners include water-soluble polymers which exhibit pseudoplastic and/or thixotropic properties in an aqueous medium such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, alkali metal salts of poly(meth)acrylate, and the like. As suitable thickeners, including thixotropes, there may also be mentioned attapulgite-type clay, silica, fumed silica, carrageenan, croscarmellose sodium, furcelieran, glycerol, hydroxypropyl methylcellulose, polystyrene, vinylpyrrolidone/styrene block copolymer, hydroxypropyl cellulose, hydroxypropyl guar gum, and sodium carboxymethylcellulose. Xanthan gum is preferred.

In the case of bioactive agrichemical compositions that are or may be subject to freezing during storage or use, especially aqueous and aqueous-based concentrates and solutions, it is desirable to add antifreeze additives. Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like. As a particular subset of suitable antifreeze materials there can be mentioned ethylene glycol, propylene glycol and glycerin.

It is possible to use dyes such as inorganic pigments, such as, for example: iron oxides, titanium oxides, Prussian blue; organic dyestuffs, such as those of the alizarin, azo or metal phthalocyanin type; or of trace elements such as iron, manganese, boron, copper, cobalt, molybdenum or zinc salts. The use of such dyes enables one to determine which areas and substrates, including plants, have been treated with the bioactive composition. Such marking is especially important for a variety of applications and reasons. For example, the use of dyes in seed treatments will enable a quick visual determination of which seeds have and have not been treated. Similarly, in disinfectant applications, for example in a biotechnology laboratories, microbiology laboratories, food and/or pharmaceutical manufacturing and processing facilities and the like, the use of they dye, will allow those performing the cleaning operation to ensure that all surfaces are treated. Here, for example, the material could be applied and allowed to sit for a brief period before being wiped to leave the cleaned surface. Further, in aerial, drop or broadcast application, it enables the pilot or driver of the dispensing vehicle see what areas have already been treated.

Although not all additives and adjuvants have been described above, those skilled in the art, particularly in the art pertinent to the specific end-use application anticipated, will certainly appreciate what other ingredients, additives and the like would or should be used for their application. The amount by which each additive is to be incorporated into the compositions will, once again, depend upon the end-use application and the method of application and environment into which it is to be employed. Generally, though, the selection and amount is that which is conventional for such additives in such applications. However, with the selection of any additives, it is important to ensure that they will not interfere with the bioactivity of the compositions of the present invention or that any such interference will be minimized so as to enable one to take the most advantage of the bioactive compositions of the present invention. Those skilled in the art, based upon the teachings set forth herein and in the following examples, will appreciate where attention is due and, in any event, such can be addressed by simple screening applications.

As noted above, it is important to avoid the use of conventional bioactive agrichemical actives as well as any other additives and components, including those of the types mentioned above, that interfere with or adversely affect the bioefficacy of the compositions according to the present invention. Most especially, it is important to avoid the use of those agrichemical actives and other additives or compounds that are known to or will likely irreversibly or strongly sequester, bind, or complex with the antimicrobial metal ions in solution. In following, not intending to be bound by theory, it is believed that retention of the antimicrobial metal ionic charge is important for maintaining bioefficacy. For example, especially with respect to copper ions, it is best to avoid the use of ammonium salts such as ammonium sulphate, ammonium chloride, ammonium citrate, ammonium phosphate. To the extent any such materials are present or to be used their use or, more accurately, the amount thereof, should be minimized and/or the metal ion concentration increased to offset the loss of free ions in solution compounds.

The compositions of the present invention may be made by any known method for formulating agrichemical compositions, especially antimicrobial and antifungal type compositions. Generally speaking, whether making a concentrate or the application ready bioactive agrichemical compositions of the present invention or whether making a liquid system or a solid system, the bioactive acid solution or, if applicable, the solid bioactive acid composition is prepared before the addition of a conventional bioactive agrichemical active or formulation and/or other conventional agrichemical additives and agents.

The bioactive acid solution may be prepared in a number of conventional ways. For example, each component may be dissolved in the appropriate solvent, most notably water or a water-based solvent, and the solutions combined in the appropriate proportions. To some extent, the sequence of the addition and whether a pre-concentrate of the acid in the solvent is formed depends upon the solubility of the solids themselves. Preferably, the acid is initially dissolved in the appropriate solvent to the desired concentration. Where one is intending to form a concentrate, the amount of acid to be dissolved in the solvent should be such that the acid concentration is at least 40 percent and preferably form 40 to 80 percent. The antimicrobial metal ion source or sources are then dissolved in the concentrated acidic solution. This method may also be used in preparing a non-concentrated bioactive agrichemical composition where the rate at which the antimicrobial metal ion source or sources dissolves is increased with higher acid concentration. For example, as mentioned above, where the metal ion source is an antimicrobial metal ion containing ion-exchange type agent, especially those whose core is a zeolite, the use of concentrated acids has been found to readily dissolve the zeolite. Thereafter, the concentrated solution is merely diluted to the desired concentration after the solids are dissolved.

Where there is difficulty in dissolving the antimicrobial metal source or sources in the concentrated or dilute acid solution, or the rate is undesirably slow, the antimicrobial metal ion source or sources may first be dissolved in water or another suitable aqueous-based solvent and that combined with the formed acid solution. Here, the acid solution is preferably of a higher concentration than intended in the bioactive acid solution so as to account for the dilution upon adding the dissolved antimicrobial metal ion source or sources.

Similarly, whether preparing concentrates or final, end-use formulations, may be desirable to make individual stock solutions of each of the components of the bioactive acid solution which stock solutions are then combined in the appropriate proportions. Again, the concentration of each stock solution would be tailored to account for the dilution upon their combination. Obviously, far forming concentrates, the stock solutions will typically be of higher concentration than might otherwise be necessary if using the stock solutions for preparing the final, end-use diluted formulations.

In each of the foregoing instances, the solvent/solutions may be heated and are preferably agitated to expedite the dissolving of the solids in the liquid system. Furthermore, while the dissolution of antimicrobial metal ion source or sources is perhaps the simplest and most cost effective method of the preparation of the bioactive acid solutions, these bioactive acid solutions may also be prepared by, e.g., electrolytically generating the metal ion in acid solutions as seen in Arata et. al. (U.S. Pat. No. 6,197,814; US 2003/0198689A1, US 200310178374A1; US2005/0245605A1 and US2006/0115440A1, all of which are incorporated herein by reference in their entirety) or by high temperature and pressure as seen in Cummins et. al. (U.S. Pat. No. 7,192,618, incorporated herein be reference).

The surfactants may be added to the bioactive acid solution or the concentrate or may be added concurrent with or subsequent to the combination of the bioactive acid solution with the conventional bioactive agrichemical composition.

When desiring to make a liquid bioactive acid solution concentrate, one may prepare the highly concentrated solution as discussed above or make a somewhat diluted form which is then further concentrated by allowing some of the solvent to evaporate. This is particularly beneficial where the antimicrobial metal ion source or sources and/or the surfactants and/or other constituents are not soluble in and/or or are not sufficiently and/or expeditiously dissolved in the acid solution.

Depending upon the ultimate form of the inventive bioactive agrichemical composition, it may likewise be desirable to prepare a solid bioactive acid composition concentrate. These solid bioactive acid composition concentrates may also be made in a number of ways. For example, the acid, the antimicrobial metal ion source or sources and, if present, the surfactant can be dry blended. Dry blending is still possible even if the surfactant or one of the surfactants is a liquid since the amount employed is so low and will be adsorbed or absorbed by the dry materials. The dry blended materials may be employed as is or are preferably compressed to form granules. Alternatively, the solid bioactive acid composition concentrate can be formed by first preparing the bioactive acid solution concentrate mentioned above, using a volatile solvent, e.g., water or a water-base solvent, and then allowing the solvent to evaporate to leave the solid material. As necessary, the solid material is then crushed or ground to form small particles, powder or granules, of the solid bioactive acid composition.

The solid bioactive acid composition concentrate may be used to form the liquid bioactive acid solution as a concentrate or as its final, end-use diluted form. In the former, the solid concentrate is dissolved in as minimal a volume of an appropriate solvent, notably water or a water based solvent, to form the concentrate. If need be or desired, especially if dissolving is hastened, a larger volume of the solvent may be employed and then partially evaporated to concentrate the materials.

Solid bioactive acid compositions in their final, end-use dilution may be prepared by dry blending the acid, the antimicrobial metal ion source or sources and the surfactant with a solid filler material or the aforementioned solid bioactive acid composition concentrate may be let down or diluted with solid filler materials. Alternatively, and preferably, the solid bioactive acid composition is prepared by treating a filler material with a bioactive acid solution. Here the liquid bioactive acid solution is applied to or combined with the filler material, which is preferably in particle form, and is adsorbed by and/or absorbed by the particles of the filler. For example, a mist of the bioactive acid solution may be sprayed or a steady or intermittent stream of the bioactive acid solution may be poured onto the particles as they are tumbled, stirred, etc. This embodiment has the added advantage that the amount or concentration of liquid acid solution applied to the adsorbent or absorbent carrier or conventional bioactive agrichemical active for formulated active can be higher than would be applied in the liquid diluted state so as to allow for longer term bioefficacy. In essence, the treated carrier or conventional active serves as a reservoir of the bioactive components of the liquid acid solution.

Given the high transportation costs and the ease of dilution, it is most preferable and cost effective to prepare concentrates, especially liquid concentrates, of the inventive bioactive agrichemical compositions which concentrates are then diluted or let down at the time of application. These liquid concentrates are then diluted or let down with an appropriate solvent, especially water or a water based solvent, to the desired concentration for application.

The bioactive agrichemical compositions of the present invention have a myriad of agricultural and horticultural applications including as fungicides, bactericides, and/or plant, stramenophile and fungi-like protisticides and may be applied to seeds, soils, plants, trees, and the like. These compositions show particular promise as fungicides, bactericides, and plant, stramenophile and fungi-like protisticides due to their unique and surprising strong bioefficacy at extremely low levels of antimicrobial metals, For example, the use of these materials allows for effective rates of applications wherein, for example, the amount of copper to be applied is on the order of grams per acre, not kilograms as is necessary with conventional copper and copper based fungicides.

Besides the marked bioefficacy at such low levels of antimicrobial metal ion, another attribute of the inventive bioactive agrichemical compositions is that they have no or little phytotoxicity. This is especially important since a bioeffective material that severely damages or kills the plant concurrent with killing the target organism is of little use unless one is not concerned with losing a crop and is most interested in controlling the target organism before it gets out of control. Another important and beneficial factor associated with the inventive compositions is the fact that they do not and are not likely to induce or be associated with any resistance in the target organisms. This contrasts sharply with the use of organic bioactive agrichemicals, especially fungicides and antibiotics, for which studies and actual commercial practice has shown a marked and growing tendency of resistance among the targeted organisms, even within a few years or less of their first use. The development of such bioactive agrichemical resistant microorganisms, while bothersome at the present time, could lead to catastrophic results if unchecked.

Typically, the rate of application of the inventive bioactive agrichemical compositions of the present invention is such that the total amount of antimicrobial metal ions (as metal) originated from the dissolved antimicrobial metal ion source or sources applied per acre will be about 200 grams or less, preferably 100 grams or less, more preferably 50 grams or less, most preferably 20 grams or less. Of course the specific application rate and, thus, the total amount applied per acre, will vary from target organism to target organism, from one form to another and from one application method to another. Indeed, suitable rates may be such that the total metal ion (as metal) may be on the order of 5 grams per acre, even on the order of fractions of a gram per acre, perhaps as low as 0.5 grams per acre or even 0.05 grams per acre. While higher loadings, higher than 200 grams per acre, may provide even greater or faster bioefficacy, the trade-off of increased environmental, health and safety concerns does not generally warrant or is not typically justified by the increased, oftentimes nominal increase, in bioefficacy.

The bioactive agrichemical compositions of the present invention may be applied to any number of agricultural, including horticultural, crops including ornamental plants, shrubs and trees; flowering plants; fruiting trees, vegetable crops; feed crops; ornamental grasses and turf; etc. Exemplary crops that are of particular concern due to their significant economic and food source impact include soy beans, tomatoes, potatoes, apples, peanuts, grapes, almonds, sugarbeets and citrus. Diseases and microorganisms to be targeted by the bioactive agrichemical compositions of the present invention include, but are not limited to citrus canker; soybean rust; leaf, stem and stripe rusts; leaf blights; early blights; late blights; fire blight; leaf spots; powdery mildew; bacterial canker; early rot; *Alternaria* leaf blight; *Alternaria* leaf spot; *Fabrea* leaf spot; bacterial wilt; Pierce's disease; Karnal bunt; citrus greening; potato, wart; *Agrobacterium tumefaciens; clavibacter michiganensis; Pseudomonas syrinhea; fusarium; phytophthora infestans; Alternaria solani; Erwinia arnylovora; Botrytis cinerea; Xanthomonas vesicatoria;* and the like. A more comprehensive listing of specific pathogens and the crops they attack are set forth in Tate—US 2005/0079227A1, the contents of which are hereby incorporated herein by reference.

These compositions may be applied in any conventional manner, spraying, dusting, spreading, etc., as also noted above. Typically any given formulation will be applied in the manner consistent for the targeted crop and microorganism. Furthermore, it is also contemplated that any conventional bioactive agent or other agrichemical additive, if any, to be used may be applied individually, concurrently or sequentially (essentially as a two-part system), within a few hours of each other, preferably within an hour or two of each other, particularly where there is concern that the conventional bioactive agent or other agrichemical additive may interfere with the performance of the bioactive acid solution or composition of the present invention, e.g., adversely sequester or bind the antimicrobial metal ions. Typically though, especially for convenience and cost savings, the inventive agrichemical compositions of the present invention will be applied as a single composition.

Unlike disinfectants where bioefficacy is measured in terms of log kill, particularly within specified time period, the bioefficacy of the bioactive agrichemical compositions of the present invention is more so represented or evidenced by an increase in yields or reduction in loss of the crop. Even a 10% improvement in yield can have a significant economic impact. In essence, even a seemingly minor reduction in the target organism or a modest inhibition in the growth or proliferation of the target organism can manifest an acceptable bioefficacy. Furthermore, the duration of this effect need not be long-lived, for example, efficacy over a couple of days or so may be sufficient. Generally, and preferably, it is desirable to see a significant reduction, 25% or more, preferably 50% or more, in the growth or proliferation of the target organism over, two or more, preferably four or more days. More preferably, it is desirable to see a 85% or more, most preferably a 95% or more, reduction in the growth or proliferation of the target organism over two or more, most preferably four or more days. Again, though, from a commercial perspective, the desired outcome is an increase, at least a 10% increase, preferably at least a 30% increase, most preferably a 65% increase, in yield as compared to the untreated crop.

The following examples are presented as demonstrating the bioefficacy of the bioactive agrichemical compositions according to the present invention as well as the unexpected synergy resulting from the use of the bioactive acid solutions or bioactive acid compositions in combination with conventional bioactive agrichemical actives and formulated actives—the latter being the subject matter of the aforementioned International and United States co-pending and co-filed patent applications. These examples are merely illustrative of the invention and are not to be deemed limiting thereof. Those skilled in the art will recognize many variations that are within the spirit of the invention and scope of the claims.

*Saccharomycetes Cerevisiae* Studies

A series of experiments (Examples 1-269 below) were conducted to evaluate the performance of the individual components of the claimed bioactive compositions as well as various combinations thereof, including, the claimed compositions themselves, in suppressing the growth of *Saccharomycetes Cerevisiae* (Fleishmann's Bakers yeast). *Saccharomycetes Cerevisiae* was selected as a test organism as it is generally accepted in the industry as an indicator or surrogate organism for a wide variety of fungi. In each of these experiments, the same general procedure was followed unless otherwise indicated.

Experimental Detail: A growth medium was prepared by adding 10 grams of nutrient medium (Difco Sabouraud dextrose broth from BD of Franklin Lakes, N.J., USA) to 300 ml of distilled water. Fleishmann's Bakers yeast was then added to the growth medium while mixing using a magnetic stirrer until a uniform dispersion was obtained having an initial turbidity of between about 50 and 100 NTU as measured using a HF Instruments ORT 100B Turbidity Meter. Once the appropriate dispersion was obtained, 20 ml aliquots were then dispensed, with continued mixing, into 40 ml borosilicate glass vials with Teflon lined caps (MR International Cat. No. 15900-004). The system/component to be evaluated was then added to the vial and intimately shaken to ensure a good, substantially homogeneous mixture. The turbidity of each mixture was then determined and the vial transferred to an incubator at 30° C. Each vial was periodically removed from the incubator and the mixture in the vials assessed for turbidity: the specific timing for such evaluation was as set forth in the discussion of the experiments and the accompanying tables.

In each experiment, unless otherwise specified, a 2 ml aqueous solution containing the specified bioactive system or component thereof was added to the 20 ml yeast suspension and mixed thoroughly. Typically the surfactants were added separately in a concentrated solution in water; however, the volume added was negligible: a fraction of an ml. For convenience in understanding efficacy levels, the amounts or concentrations of the various components presented in each of the following tables and experiments are of the diluted material in the test vial: not of the concentrate added to the test vial. Furthermore, the concentrations presented are on the basis of a 20 ml total volume, not the actual 22+ ml volume. Multiplying each of the listed concentrations by 0.9 (or 0.95 with those compositions using 1 ml aqueous solutions) will provide a more accurate assessment of the concentrations of the various components evaluated, i.e., a 5 ppm silver concentration is actually closer to 4.5 ppm. Finally, for those vials to which no bioactive system or component thereof was added (the controls) or which only contained the surfactants, 2 ml of additional growth medium was added to ensure relative equivalent dilutions of the yeast.

In the tables below, the results are presented as the actual turbidity readings (NTU) with a sub-table presenting the change or delta in NTU values. Given the nature of the system, changes in turbidity are reflective of the relative performance/bioefficacy of the bioactive systems and their components. In certain instances, a high level of bioactive material, especially the metal component, caused an immediate and relatively sharp increase in optical density or turbidity. This was believed to have been a result of lysing of at least a portion on the yeast cells themselves. Consequently, especially in those examples having a high level of bioactive, it is equally, if not more, important to look at the change in turbidity from either the half hour or one hour turbidity results, if presented, forward, not from time zero.

Examples 1-21

Acid Concentration

A first series of experiments was conducted for evaluating the performance of various antimicrobial metals and combinations of such metals, with and without citric acid and with and without sodium lauroyl sarcosinate anionic surfactant. Each of the metals was added in the form of an aqueous solution of their citrate salts, namely, silver citrate, copper citrate and zinc citrate,

TABLE 1

| Example | Metal Ion and Amount (ppm) | Citric Acid (wt %) | Na Lauroyl Sarcosinate (wt %) | Turbidity (NTU) Time zero | Time 1 Hr | T 18 hours | T 24 hours | T 96 Hours |
|---|---|---|---|---|---|---|---|---|
| 1 | Ag 5 ppm | 0 | | 44.5 | 59.6 | 890 | 932 | 995 |
| 2 | Ag 5 ppm | 1 | | 47.5 | 64 | 882 | 902 | 1044 |
| 3 | Ag 5 ppm | 2 | | 50.9 | 68.4 | 881 | 950 | 1025 |
| 4 | Ag 5 ppm | 0 | 0.005 | 46.8 | 51.5 | 596 | 677 | 673 |
| 5 | Ag 5 ppm | 1 | 0.005 | 59.4 | 68.4 | 85 | 130 | 854 |
| 6 | Ag 5 ppm | 2 | 0.005 | 70.9 | 75 | 85 | 120 | 880 |
| 7 | Zn 5 ppm | 0 | | 43.8 | 64.5 | 992 | 993 | 1051 |
| 8 | Zn 5 ppm | 1 | | 46.6 | 66.5 | 934 | 962 | 1027 |
| 9 | Zn 5 ppm | 2 | | 49.5 | 71 | 936 | 1038 | 1063 |
| 10 | Zn 5 ppm | 0 | 0.005 | 45.9 | 63 | 656 | 747 | 712 |
| 11 | Zn 5 ppm | 1 | 0.005 | 57 | 71 | 160 | 223 | 744 |
| 12 | Zn 5 ppm | 2 | 0.005 | 73 | 76.5 | 105 | 119 | 466 |
| 13 | Cu 5 ppm | 0 | | 45.6 | 68 | 940 | 1021 | 1100 |
| 14 | Cu 5 ppm | 1 | | 49 | 72 | 940 | 1018 | 1102 |
| 15 | Cu 5 ppm | 2 | | 49 | 74 | 900 | 973 | 1100 |
| 16 | MI1 | 0 | 0.005 | 39 | 44.5 | 449 | 575 | 658 |
| 17 | MI1 | 1 | 0.005 | 73.9 | 87 | 100 | 105 | 732 |
| 18 | MI1 | 2 | 0.005 | 132 | 137 | 137 | 137 | 690 |
| 19 | MI1 | 1 | 0.01 | 74.5 | 74.8 | 87 | 89 | 116 |
| 20 | Control (No Biocide) | | | 53.2 | 69.4 | 1031 | 1085 | 1122 |
| 22 | Control (No Biocide) | | | 53.2 | 78 | 1101 | 1093 | 1128 |

*MI1 a 4% citric acid solution containing of 50 ppm each of Ag, Cu and Zn per ml giving ~5 ppm of each in the test vial

TABLE 1A

| Example | Metal Ion and Amount (ppm) | Citric Acid (wt %) | Na Lauroyl Sarcosinate (wt %) | Change in Turbidity from $T_0$ (delta NTU) Time 1 Hr | T 18 hours | T 24 hours | T 96 Hours |
|---|---|---|---|---|---|---|---|
| 1 | Ag 5 ppm | 0 | | 15.1 | 845.5 | 887.5 | 950.5 |
| 2 | Ag 5 ppm | 1 | | 16.5 | 834.5 | 854.5 | 996.5 |
| 3 | Ag 5 ppm | 2 | | 17.5 | 830.1 | 899.1 | 974.1 |
| 4 | Ag 5 ppm | 0 | 0.005 | 4.7 | 549.2 | 630.2 | 626.2 |
| 5 | Ag 5 ppm | 1 | 0.005 | 9 | 25.6 | 70.6 | 794.6 |
| 6 | Ag 5 ppm | 2 | 0.005 | 4.1 | 14.1 | 49.1 | 809.1 |
| 7 | Zn 5 ppm | 0 | | 20.7 | 948.2 | 949.2 | 1007.2 |
| 8 | Zn 5 ppm | 1 | | 19.9 | 887.4 | 915.4 | 980.4 |
| 9 | Zn 5 ppm | 2 | | 21.5 | 886.5 | 988.5 | 1013.5 |
| 10 | Zn 5 ppm | 0 | 0.005 | 17.1 | 610.1 | 701.1 | 666.1 |
| 11 | Zn 5 ppm | 1 | 0.005 | 14 | 103 | 166 | 687 |
| 12 | Zn 5 ppm | 2 | 0.005 | 3.5 | 32 | 46 | 393 |
| 13 | Cu 5 ppm | 0 | | 22.4 | 894.4 | 975.4 | 1054.4 |
| 14 | Cu 5 ppm | 1 | | 23 | 891 | 969 | 1053 |
| 15 | Cu 5 ppm | 2 | | 25 | 851 | 924 | 1051 |
| 16 | MI1 | 0 | 0.005 | 5.5 | 410 | 536 | 619 |
| 17 | MI1 | 1 | 0.005 | 13.1 | 26.1 | 31.1 | 658.1 |
| 18 | MI1 | 2 | 0.005 | 5 | 5 | 5 | 558 |
| 19 | MI1 | 1 | 0.01 | 0.3 | 12.5 | 14.5 | 41.5 |
| 20 | Control (No Biocide) | | | 16.2 | 977.8 | 1031.8 | 1068.8 |
| 21 | Control (No Biocide) | | | 24.8 | 1047.8 | 1039.8 | 1074.8 |

*MI1 a 4% citric acid solution containing of 50 ppm each of Ag, Cu and Zn per ml giving ~5 ppm of each in the test vial or, in the case of Examples 16-19, as a mixture of all three citrate salts (Mi1). The specific formulations evaluated and the resultant yeast growth study results are shown in Tables 1 and 1A.

As seen in Tables 1 and 1A, those formulations having both the acid and the anionic surfactant provided marked yeast growth inhibition through at least the first 24 hour period, even with the low lever of anionic surfactant. Those samples with just the metal ion or the metal ion in combination with the acid had no appreciable effect on yeast growth. Although some inhibition was also noted in those samples wherein only the metal(s) and surfactant were present, the inhibition was not appreciable. Rather, as noted, the further presence of excess acid gave a marked and unexpected level of improvement. Finally, that formulation having all three antimicrobial metal ions, plus the acid and surfactant provided continued to show excellent yeast growth inhibition even at the 96 hour test limit.

Examples 22-42

Surfactant Evaluation

A similar series of experiments was conducted again to evaluate the performance of various combinations of the components of the bioactive compositions of the present invention as well as to demonstrate other anionic surfactants and combinations of surfactants. The specific formulations evaluated and the yeast growth results are presented in Tables 2 and 2A.

Once again, the importance of all three constituents was evident from the results shown in Tables 2 and 2A. These results further confirm that even a low excess acid content, here 0.4%, provides excellent inhibition in yeast growth through 96 hours. The somewhat less than ideal results shown in Examples 26 and 29 suggest some variation amongst anionic surfactants, at least with sodium lauryl sulfate (SLS), with zinc and copper ions. However, the results are still significantly better than without a surfactant at all and suggest a possible synergy with two. Furthermore, because of the easier solubility of the SLS, as compared to the sodium lauroyl sarcosinate (NaLS), the presence of the SLS helps improve and/or enhance the solubility of the NaLS under acid conditions.

Examples 43-57

Low Concentration Evaluation

A series of experiments were conducted again to evaluate the performance of various combinations of the components of the bioactive compositions of the present invention, this time focusing on the impact of the low concentrations of the components and their combinations. In this set of experiments, 1 ml aqueous solutions of the bioactive/citric acid components were added to the 20 ml vials. The specific formulations evaluated and the yeast growth results are presented in Tables 3 and 3A.

As seen in Tables 3 and 3A, once again the combination of bioactive metal ions, citric acid and anionic surfactant demonstrated a marked inhibition in yeast growth as compared to the individual components, even at the low concentrations of excess acid and surfactant. Though, once again, the

TABLE 2

| | | | Turbidity (NTU) | | | | |
|---|---|---|---|---|---|---|---|
| Example | Metal citrates (ppm) in .4% citric acid | Surfactant* (wt %) | Time zero | T 1 hour | T 18 hours | T 24 hours | T 96 Hrs |
| 22 | Copper 5 ppm | | 103 | 114 | 410 | 463 | 588 |
| 23 | Zinc 5 ppm | | 103 | 118 | 475 | 488 | 589 |
| 24 | Silver 5 ppm | | 155 | 168 | 181 | 190 | 670 |
| 25 | Copper 5 ppm | .005 NaLS | 145 | 146 | 157 | 160 | 149 |
| 26 | Copper 5 ppm | .005 SLS | 119 | 128 | 252 | 326 | 502 |
| 27 | Copper 5 ppm | .005 NaLS:.005 SLS | 145 | 144 | 156 | 154 | 157 |
| 28 | Zinc 5 ppm | .005 NaLS | 148 | 156 | 157 | 157 | 157 |
| 29 | Zinc 5 ppm | .005 SLS | 126 | 134 | 217 | 234 | 539 |
| 30 | Zinc 5 ppm | .005 NaLS:.005 SLS | 155 | 155 | 157 | 157 | 158 |
| 31 | Silver 5 ppm | .005 NaLS | 170 | 170 | 184 | 184 | 180 |
| 32 | Silver 5 ppm | .005 SLS | 177 | 177 | 193 | 196 | 196 |
| 33 | Silver 5 ppm | .005 NaLS:.005 SLS | 193 | 190 | 198 | 199 | 199 |
| 34 | Copper 2.5 ppm:Zinc 2.5 ppm | | 99 | 109 | 498 | 510 | 614 |
| 35 | Copper 2.5 ppm:Silver 2.5 ppm | | 128 | 152 | 424 | 530 | 727 |
| 36 | Zinc 2.5 ppm:Silver 2.5 ppm | | 128 | 151 | 541 | 621 | 720 |
| 37 | Control 1 (no biocide) | | 91 | 114 | 560 | 580 | 754 |
| 38 | Control 2 (no biocide) | | 91 | 114 | 563 | 584 | 726 |
| 39 | Copper 2.5 ppm:Zinc 2.5 ppm | .005 NaLS:.005 SLS | 192 | 180 | 193 | 193 | 193 |
| 40 | Copper 2.5 ppm:Silver 2.5 ppm | .005 NaLS:.005 SLS | 181 | 204 | 205 | 206 | 206 |
| 41 | Zinc 2.5 ppm:Silver 2.5 ppm | .005 NaLS:.005 SLS | 194 | 193 | 212 | 212 | 212 |
| 42 | Copper 2.5 ppm:Silver 2.5 ppm:Zinc 2.5 ppm | .005 NaLS:.005 SLS | 193 | 193 | 199 | 200 | 205 |

*NaLS—sodium lauroyl sarcosinate, SLS—sodium lauryl sulfate

TABLE 2A

| | | | Change in Turbidity from T0 (delta NTU) | | | |
|---|---|---|---|---|---|---|
| Example | Metal citrates (ppm) in .4% citric acid | Surfactant* (wt %) | T 1 hour | T 18 hours | T 24 hours | T 96 Hrs |
| 22 | Copper 5 ppm | | 11 | 307 | 380 | 485 |
| 23 | Zinc 5 ppm | | 15 | 372 | 365 | 486 |

TABLE 2A-continued

| | | | Change in Turbidity from T0 (delta NTU) | | | |
|---|---|---|---|---|---|---|
| Example | Metal citrates (ppm) in .4% citric acid | Surfactant* (wt %) | T 1 hour | T 18 hours | T 24 hours | T 96 Hrs |
| 24 | Silver 5 ppm | | 13 | 26 | 35 | 515 |
| 25 | Copper 5 ppm | .005 NaLS | 1 | 12 | 15 | 4 |
| 26 | Copper 5 ppm | .005 SLS | 9 | 133 | 207 | 383 |
| 27 | Copper 5 ppm | .005 NaLS:.005 SLS | −1 | 11 | 9 | 12 |
| 28 | Zinc 5 ppm | .005 NaLS | 8 | 9 | 9 | 9 |
| 29 | Zinc 5 ppm | .005 SLS | 8 | 91 | 108 | 413 |
| 30 | Zinc 5 ppm | .005 NaLS:.005 SLS | 0 | 2 | 2 | 3 |
| 31 | Silver 5 ppm | .005 NaLS | 0 | 14 | 14 | 10 |
| 32 | Silver 5 ppm | .005 SLS | 0 | 16 | 19 | 19 |
| 33 | Silver 5 ppm | .005 NaLS:.005 SLS | −3 | 5 | 6 | 6 |
| 34 | Copper 2.5 ppm:Zinc 2.5 ppm | | 10 | 399 | 411 | 515 |
| 35 | Copper 2.5 ppm:Silver 2.5 ppm | | 24 | 296 | 402 | 599 |
| 36 | Zinc 2.5 ppm:Silver 2.5 ppm | | 23 | 413 | 493 | 592 |
| 37 | Control 1 (no biocide) | | 23 | 469 | 489 | 663 |
| 38 | Control 2 (no biocide) | | 23 | 472 | 493 | 635 |
| 39 | Copper 2.5 ppm:Zinc 2.5 ppm | .005 NaLS:.005 SLS | −12 | 1 | 1 | 1 |
| 40 | Copper 2.5 ppm:Silver 2.5 ppm | .005 NaLS:.005 SLS | 23 | 24 | 25 | 25 |
| 41 | Zinc 2.5 ppm:Silver 2.5 ppm | .005 NaLS:.005 SLS | −1 | 18 | 18 | 18 |
| 42 | Copper 2.5 ppm:Silver 2.5 ppm:Zinc 2.5 ppm | .005 NaLS:.005 SLS | 0 | 6 | 7 | 12 |

TABLE 3

| | | | | Turbidity (NTU) | | | | |
|---|---|---|---|---|---|---|---|---|
| Example | Bioactive Metal* | Citric Acid (wt %) | Surfactant** (wt %) | OD(To) | OD (T1 hr) | OD (T18) | OD (T24) | OD (T48) |
| 43 | | | 0.01 NaLS | 43 | 45 | 550 | 613 | 521 |
| 44 | | | 0.02 NaLS | 43 | 40 | 460 | 524 | 624 |
| 45 | | | 0.01 SLS | 43 | 47 | 675 | 728 | 758 |
| 46 | | | 0.02 SLS | 37 | 42 | 495 | 610 | 605 |
| 47 | | | 0.01 NaLS/0.01 SLS | 40 | 41 | 370 | 466 | 580 |
| 48 | | | 0.005 NaLS/0.005 SLS | 43 | 47 | 630 | 696 | 726 |
| 49 | | 0.05 | | 42 | 46 | 835 | 920 | 878 |
| 50 | | 0.1 | | 38 | 44 | 780 | 864 | 852 |
| 51 | MI1 | 0.2 | | 50 | 62 | 809 | 891 | 915 |
| 52 | MI1 | 0.2 | 0.01 NaLS | 64 | 63 | 67 | 68 | 69 |
| 53 | MI1 | 0.2 | 0.01 SLS | 61 | 65 | 300 | 569 | 1039 |
| 54 | MI1 | 0.2 | 0.005 NaLS/0.005 SLS | 60 | 63 | 62 | 63 | 73 |
| 55 | MI1 | 0.2 | 0.01 NaLS/0.01 SLS | 85 | 76 | 76 | 79 | 79 |
| 56 | Control 1 | | | 43 | 51 | 960 | 997 | 939 |
| 57 | Control 2 | | | 43 | 51 | 890 | 986 | 887 |

*MI1 a 4% citric acid solution containing of 50 ppm each of Ag, Cu and Zn per ml giving (@ 1 ml) ~5 ppm of each in the test vial
**NaLS—sodium lauroyl sarcosinate, SLS—sodium lauryl sulfate

TABLE 3A

| | | | | Change in Turbidity from T0 (delta NTU) | | | |
|---|---|---|---|---|---|---|---|
| Example | Bioactive Metal* | Citric Acid (wt %) | Surfactant** (wt %) | OD (T1 hr) | OD (T18) | OD (T24) | OD (T48) |
| 43 | | | 0.01 NaLS | 2 | 507 | 570 | 478 |
| 44 | | | 0.02 NaLS | −3 | 417 | 481 | 581 |
| 45 | | | 0.01 SLS | 4 | 632 | 685 | 715 |
| 46 | | | 0.02 SLS | 5 | 458 | 573 | 568 |
| 47 | | | 0.01 NaLS/0.01 SLS | 1 | 330 | 426 | 540 |
| 48 | | | 0.005 NaLS/0.005 SLS | 4 | 587 | 653 | 683 |
| 49 | | 0.05 | | 4 | 793 | 878 | 836 |
| 50 | | 0.1 | | 6 | 742 | 826 | 814 |
| 51 | MI1 | 0.2 | | 12 | 759 | 841 | 865 |
| 52 | MI1 | 0.2 | 0.01 NaLS | −1 | 3 | 4 | 5 |
| 53 | MI1 | 0.2 | 0.01 SLS | 4 | 239 | 508 | 978 |
| 54 | MI1 | 0.2 | 0.005 NaLS/0.005 SLS | 3 | 2 | 3 | 13 |
| 55 | MI1 | 0.2 | 0.01 NaLS/0.01 SLS | −9 | −9 | −6 | −6 |
| 56 | Control 1 | | | 8 | 917 | 954 | 896 |
| 57 | Control 2 | | | 8 | 847 | 943 | 844 |

*MI1 a 4% citric acid solution containing of 50 ppm each of Ag, Cu and Zn per ml giving (@ 1 ml) ~5 ppm of each in the test vial
**NaLS—sodium lauroyl sarcosinate, SLS—sodium lauryl sulfate surfactants appeared to have a marginal inhibitory effect, as compared to the controls, on their own, the inhibition was negligible as compared to that of the systems according to the present invention.

Examples 58-71

Ion-Exchange Metal Ion Source

A metal citrate solution was prepared by adding approximately 4 grams of citric acid to about 8 grams of water and mixed until fully dissolved. Thereafter, 0.1 grams each of two ion-exchange type antimicrobial agents, AgION AC10D and AgION AK10D antimicrobial agents from AgION Technologies of Wakefield, Mass., USA, were added to the concentrated citric acid solution with agitation until the antimicrobial agents fully dissolved. Approximately 92 grams of water was then added to provide a 4% citric acid solution having dissolved therein 0.1 wt % AC10D and 0.1 wt % AK10D. AgION AK10D contains about 5.0% by weight silver and about 13% by weight zinc and AgION AC10D contains about 6.0% by weight copper and about 3.5% by weight silver. Various quantities of the so formed citric acid solution were then added to test vials so as to provide a silver content in the test vials of approximately 1.25 ppm, 2.5 ppm, 5.0 ppm and 10 ppm. Additionally, different surfactant and surfactant combinations were added to certain vials to demonstrate the effect of different metal and acid contents on bioefficacy with and without surfactants. The specific formulations evaluated and the yeast growth results are presented in Tables 4 and 4A.

As seen in Tables 4 and 4A, the compositions according to the present invention provided marked inhibition in yeast growth. Although Example 61 containing the higher concentration of metal ions (10 ppm silver, 7 ppm copper and 15.3 ppm zinc), showed good yeast growth inhibition, the higher degree of efficacy comes with the concomitant increase in the release of these metals into the environment. This becomes especially important where the bioactive materials are to be used in or near marine and/or agricultural applications. Thus, while high metal concentrations, especially of silver, will provide better bioefficacy, they also hasten the impact on aquatic environments. On the other hand, as shown in those examples employing the antimicrobial metal containing acid solutions with the anionic surfactant, especially sodium lauroyl sarcosinate, alone

TABLE 4

| | | | Turbidity (NTU) | | | | | |
|---|---|---|---|---|---|---|---|---|
| Example | Ag Concentration ppm | Surfactant* (wt %) | OD(T zero) | OD(T1 hr) | OD(T18 hr) | OD(T24 hr) | OD(T44 hr) | OD(T120 hr) |
| 58 | 1.25 | | 108 | 128 | 913 | 880 | 954 | 1136 |
| 59 | 2.5 | | 127 | 157 | 865 | 890 | 941 | 1024 |
| 60 | 5 | | 176 | 199 | 229 | 227 | 234 | 721 |
| 61 | 10 | | 168 | 173 | 191 | 191 | 190 | 180 |
| 62 | 1.25 | 0.005 NaLS | 143 | 158 | 240 | 560 | 843 | 708 |
| 63 | 2.5 | 0.005 NaLS | 180 | 179 | 204 | 210 | 729 | 843 |
| 64 | 5 | 0.005 NaLS | 194 | 201 | 222 | 221 | 227 | 227 |
| 65 | 1.25 | 0.005 SLS | 136 | 167 | 953 | 930 | 973 | 1132 |
| 66 | 2.5 | 0.005 SLS | 201 | 212 | 880 | 880 | 967 | 1145 |
| 67 | 5 | 0.005 SLS | 248 | 247 | 272 | 272 | 296 | 297 |
| 68 | 1.25 | .0025 NaLS/.0025 SLS | 166 | 180 | 343 | 730 | 957 | 986 |
| 69 | 2.5 | .0025 NaLS/.0025 SLS | 215 | 217 | 235 | 239 | 759 | 940 |
| 70 | 5 | .0025 NaLS/.0025 SLS | 235 | 235 | 257 | 255 | 259 | 268 |
| 71 | Control | | 101 | 125 | 1050 | 1050 | 1040 | 1183 |

*NaLS—sodium lauroyl sarcosinate, SLS—sodium lauryl sulfate

TABLE 4A

| | | | Change in Turbidity (delta NTU) | | | | |
|---|---|---|---|---|---|---|---|
| Example | Ag Concentration ppm | Surfactant* (wt %) | OD(T1 hr) | OD(T18 hr) | OD(T24 hr) | OD(T44 hr) | OD(T120 hr) |
| 58 | 1.25 | | 20 | 805 | 772 | 846 | 1028 |
| 59 | 2.5 | | 30 | 738 | 763 | 814 | 897 |
| 60 | 5 | | 23 | 53 | 51 | 58 | 545 |
| 61 | 10 | | 5 | 23 | 23 | 22 | 12 |
| 62 | 1.25 | 0.005 NaLS | 15 | 97 | 417 | 700 | 565 |
| 63 | 2.5 | 0.005 NaLS | −1 | 24 | 30 | 549 | 683 |
| 64 | 5 | 0.005 NaLS | 7 | 28 | 27 | 33 | 33 |
| 65 | 1.25 | 0.005 SLS | 31 | 817 | 794 | 837 | 996 |
| 66 | 2.5 | 0.005 SLS | 11 | 679 | 679 | 766 | 944 |
| 67 | 5 | 0.005 SLS | −1 | 24 | 24 | 48 | 49 |
| 68 | 1.25 | .0025 NaLS/.0025 SLS | 14 | 177 | 564 | 791 | 820 |
| 69 | 2.5 | .0025 NaLS/.0025 SLS | 2 | 20 | 24 | 544 | 725 |
| 70 | 5 | .0025 NaLS/.0025 SLS | 0 | 22 | 20 | 24 | 33 |
| 71 | Control | | 24 | 949 | 949 | 939 | 1082 |

*NaLS—sodium lauroyl sarcosinate, SLS—sodium lauryl sulfate or in combination with sodium lauryl sulfate, the same and even better yeast inhibition is realized with less than half, even less than one-quarter, the metal ion concentrations. Furthermore, these results show that by adjusting the level of surfactant, one may reduce the level of metal ion even more while still providing marked inhibition of the fungi.

Also surprising about this example is the finding that citric acid could dissolve the antimicrobial zeolite particles. This finding presents another means by which the inventive compositions may be made as well as a number of alternative applications for such materials not otherwise possible with the zeolites in their solid form.

Examples 72-79

Metal Concentration

For this study a concentrated bioactive system (MI2) was prepared comprising a 16% aqueous citric acid solution having dissolved therein silver citrate, copper citrate and zinc citrate, each added in an amount to provide 200 ppm of each metal, together with 015% sodium Lauroyl sarcosinate and 0.32% sodium lauryl sulfate. Various amounts of this system were added to the test vials to further assess the impact of metal concentration yeast inhibition. A further example was prepared further including a non-ionic surfactant, Tween 20 (polyoxyethylene (20) sorbitan monolaurate), an emulsifier to assess its impact on performance. The specific formulations evaluated and the results are presented in Tables 5 and 5A.

As seen in Tables 5 and 5A, the high concentrations of metals dramatically inhibited, if not stopped altogether, yeast growth. The solutions of Examples 76, 77 and 78 containing ultra-high metal content appeared to destroy the yeast cells, showing what appeared to be a rapid denaturation of the yeast on addition of the bioactive material to the text vials. It is likely that the initial high turbidity reflected both that arising from the addition of the bioactive materials themselves as well as the destruction of the yeast cells.

Regardless, the results show that marked inhibition is also attained at much lower concentrations of the metal in the presence of the excess acid and surfactant. Indeed, just 15 ppm metals (5 ppm of each) provide excellent inhibition through 82 hours and beyond.

TABLE 5

| Example | MI2* added (ml) | Concentration of each metal (ppm) | Turbidity (NTU) | | | | | |
|---|---|---|---|---|---|---|---|---|
| | | | T 0 | T 18 | T 22 | T 24 | T 64 | T 82 |
| 72 | 0 | 0 | 63 | 920 | 980 | 964 | 1020 | 1050 |
| 73 | 0.1 | 1 | 81 | 608 | 722 | 820 | 1077 | 1062 |
| 74 | 0.25 | 2.5 | 111 | 126 | 142 | 160 | 752 | 810 |
| 75 | 0.5 | 5 | 145 | 198 | 208 | 208 | 205 | 203 |
| 76 | 1.0 | 10 | 483 | 410 | 395 | 369 | 320 | 300 |
| 77 | 2.0 | 20 | 1295 | 820 | 714 | 660 | 399 | 264 |
| 78 | 3.0 | 30 | 1435 | 766 | 620 | 555 | 340 | 340 |
| 79 | 0.5+ | 5 | 141 | 249 | 405 | 600 | 1116 | 1129 |

*MI2 a 16% citric acid solution containing of 200 ppm each of Ag, Cu and Zn per ml
+this formulation also contained 0.1 wt % Tween 20 a non-ionic surfactant

TABLE 5A

| Example | MI2* added (ml) | Concentration of each metal (ppm) | Change in Turbidity (delta NTU) | | | | |
|---|---|---|---|---|---|---|---|
| | | | T18-T0 | T22-T0 | T24-T0 | T64-T0 | T82-T0 |
| 72 | 0 | 0 | 857 | 917 | 901 | 957 | 987 |
| 73 | 0.1. | 1 | 527 | 641 | 739 | 996 | 981 |
| 74 | 0.25 | 2.5 | 15 | 31 | 49 | 641 | 699 |
| 75 | 0.5 | 5 | 53 | 63 | 63 | 60 | 58 |
| 76 | 1.0 | 10 | −73 | −88 | −114 | −163 | −183 |
| 77 | 2.0 | 20 | −475 | −581 | −635 | −896 | −1031 |
| 78 | 3.0 | 30 | −669 | −815 | −880 | −1095 | −1095 |
| 79 | 0.5+ | 5 | 108 | 264 | 459 | 975 | 988 |

*MI2 a 16% citric acid solution containing of 200 ppm each of Ag, Cu and Zn per ml
+this formulation also contained 0.1 wt % Tween 20 a non-ionic surfactant Finally, the addition of Tween 20 surfactant appeared to be antagonistic to the action of the bioactive systems of the present invention resulting in a reduction in the level of yeast inhibition. Still, this composition (Example 79) manifested moderate yeast inhibition through 24 hours. Depending upon the specific end-use application contemplated, it is evident that routine preliminary evaluations should be conducted before formulating with various additives to ascertain their impact on the inventive systems of the present invention.

Examples 80-95

Bioactives Synergy

A series of experiments were conducted in which possible synergies were evaluated between the inventive compositions and other bioactive materials as well as between such other bioactive materials including a fungicide, an antimicrobial agent and a disinfectant. The inventive bioactive system employed in this set of experiments (MI3) was a 4% aqueous citric acid solution containing 50 ppm silver, 50 ppm copper and 50 ppm zinc.

The fungicide evaluated was Mancozeb Flowable with Zinc from Bonide Products, Inc. of Oniskany, N.Y., USA, a commercial formulated fungicide containing 37% by wt mancozeb. Although the specific formulation of the Mancozeb product is proprietary, as a commercial formulation it would also contain certain surfactants for enabling its application to plants for efficacy. Mancozeb is an insoluble, dispersible powder that increases the turbidity of the liquids to which it is added. Nevertheless, in a separate evaluation, not reproduced here, it was found that Mancozeb was able to control or inhibit yeast growth at a concentration of about $1.23 \times 10^{-3}$. The label indicates its use rate at $2.6 \times 10^{-3}$.

The antimicrobial active evaluated was AgION AC10D, an antimicrobial zeolite additive available from AgION Technologies, Inc., of Wakefield, Mass., USA, which, as noted above, contains 6.0 M % copper and 3.5 wt % silver. In a separate dilution evaluation, not reproduced here, it was found that an aqueous suspension of AC10D showed some yeast control or inhibition at a concentration of about $6.25 \times 10^{-4}$.

Finally, the disinfectant evaluated was AgION SilverClene 24, a disinfectant material based on an aqueous solution of electrolytically generated silver citrate (~30 ppm silver), also distributed by AgION Technologies, Inc. Although proprietary, this product and its manufacture is believed to be disclosed in Arata—U.S. Pat. No. 6,583,176, which is incorporated herein by reference in its entirety.

The aforementioned materials as well as various combinations thereof were evaluated to assess their efficacy in stopping or inhibiting the growth of yeast. The specific formulations tested and the yeast inhibition results attained therewith are presented in Tables 6 and 6A.

TABLE 6

| Example | Amt MI3 (ml) | Mancozeb (wt %) | AgION AC10D (wt %) | Silver-Clene 24 (ml) | Surfactant (wt %) | Turbidity (NTU) | | | | |
|---|---|---|---|---|---|---|---|---|---|---|
| | | | | | | OD T zero | T(1 hour) | T (18 hour) | T (24 Hour) | pH |
| 80 | | 9.40E−05 | | | | 262 | 293 | 1023 | 1030 | 3.07 |
| 81 | 1 | 9.40E−05 | | | | 276 | 276 | 309 | 522 | 2.91 |
| 82 | 2 | 9.40E−05 | | | | 301 | 301 | 308 | 312 | 2.55 |
| 83 | 2 | 1.88E−04 | | | 0.05 NaLS/0.05 SLS | 350 | 362 | 362 | 362 | |
| 84 | 2 | 3.75E−04 | | | | 656 | 640 | 1001 | 1170 | 2.4 |
| 85 | 1 | 9.40E−05 | | | 0.05 SLS | 331 | 321 | 328 | 330 | 2.48 |
| 86 | to pH 6 | 3.75E−04 | | | 0.05 NaLS/0.05 SLS | 609 | 605 | 825 | 968 | 4.91 |
| 87 | | 1.88E−04 | 7.81E−05 | | 0.05 NaLS | 410 | 385 | 443 | 511 | |
| 88 | 2 | 1.88E−04 | 7.81E−05 | | 0.05 NaLS/0.05 SLS | 521 | 435 | 435 | 440 | 2.68 |
| 89 | | 9.40E−05 | | 1 | | 258 | 276 | 970 | 962 | 2.67 |
| 90 | | 1.88E−04 | | 2 | | 365 | 364 | 782 | 1048 | |
| 91 | | | 3.90E−05 | | | 128 | 151 | 862 | 800 | 3.23 |
| 92 | 2 | | 3.90E−05 | | 0.05 SLS | 154 | 156 | 172 | 175 | 2.54 |
| 93 | 2 | | 1.56E−04 | | 0.05 NaLS/0.05 SLS | 190 | 143 | 148 | 156 | 2.66 |
| 94 | 2 | | | | 0.05 NaLS/0.05 SLS | 157 | 67 | 189 | 195 | 2.51 |
| 95 | Control | | | | | 73 | 98 | 898 | 856 | 3.25 |

TABLE 6A

| Example | Amt MI3 (ml) | Mancozeb (wt %) | AgION AC10D (wt %) | Silver-Clene 24 (ml) | Surfactant (wt %) | Change in Turbidity (delta NTU) | | | | |
|---|---|---|---|---|---|---|---|---|---|---|
| | | | | | | 1 hour | 18 hour | 1-18 hour | 24 hour | 1-24 hour |
| 80 | | 9.40E−05 | | | | 31 | 761 | 730 | 768 | 737 |
| 81 | 1 | 9.40E−05 | | | | 0 | 33 | 33 | 246 | 246 |
| 82 | 2 | 9.40E−05 | | | | 0 | 7 | 7 | 11 | 11 |
| 83 | 2 | 1.88E−04 | | | 0.05 NaLS/0.05 SLS | 12 | 12 | 0 | 12 | 0 |
| 84 | 2 | 3.75E−04 | | | | −16 | 345 | 361 | 514 | 530 |
| 85 | 1 | 9.40E−05 | | | 0.05 SLS | −10 | −3 | 7 | −1 | 9 |
| 86 | to pH 6 | 3.75E−04 | | | 0.05 NaLS/0.05 SLS | −4 | 216 | 220 | 359 | 363 |
| 87 | | 1.88E−04 | 7.81E−05 | | 0.05 NaLS | −25 | 33 | 58 | 101 | 126 |
| 88 | 2 | 1.88E−04 | 7.81E−05 | | 0.05 NaLS/0.05 SLS | −86 | −86 | 0 | −81 | 5 |
| 89 | | 9.40E−05 | | 1 | | 18 | 712 | 694 | 704 | 686 |
| 90 | | 1.88E−04 | | 2 | | −1 | 417 | 416 | 683 | 682 |
| 91 | | | 3.90E−05 | | | 23 | 734 | 711 | 672 | 649 |
| 92 | 2 | | 3.90E−05 | | 0.05 SLS | 2 | 18 | 16 | 21 | 19 |
| 93 | 2 | | 1.56E−04 | | 0.05 NaLS/0.05 SLS | −47 | −42 | 5 | −34 | 13 |
| 94 | 2 | | | | 0.05 NaLS/0.05 SLS | −90 | 32 | 122 | 38 | 128 |
| 95 | Control | | | | | 25 | 825 | 800 | 783 | 758 |

The results presented in Tables 6 and 6A demonstrate a marked synergy between the inventive compositions according the present invention and commercial fungicides and antimicrobial agents. Specifically, for example, a comparison of the results for Examples 80, 81 and 82 demonstrate that combining low amounts of the metal ions, citric acid and fungicide provided excellent antifungal performance. While it is noted that these formulations did not have additional surfactant, the commercial fungicide itself contained surfactants that worked in combination with the metal ions and citric acid to provide the benefits owing to that combination as now claimed. These results show that excellent antifungal activity, as measured by yeast growth inhibition, may be attained with less than 10% of the amount of fungicide needed to inhibit yeast growth by the simple addition of low levels of acid and metal ions. As seen from Examples 91, 92 and 93, a similar synergy is shown for the inventive compositions in combination with a conventional inorganic antimicrobial agent. Here too, less than 10% of that amount of the antimicrobial agent needed when used alone, provided good antimicrobial performance when in combination with low levels of bioactive composition according to the present invention. However, the substitution of the SilverClene 24 for the inventive composition of the present invention, Examples 89 and 90, provided no apparent benefit despite the relatively high silver content.

Finally, in Example 86, ammonia was added to a portion of the MI3 solution until the solution reached a pH of 6.2 ml of this buffered solution was then employed in the experiment. This example indicates the importance of the low pH of the compositions according to the present invention in order to provide desirable performance.

Examples 96-107

Immunox Synergy

A similar study was conducted to assess the synergy between the bioactive compositions according to the present invention and a second fungicide, Immunox, a commercial fungicide containing 1.55% myclobutanil, available from Spectrum Brands Division of United Industries of Madison, Wis., USA. As a commercial formulation, this too is expected to have some surfactants content. The bioactive composition employed in this experiment was the concentrated bioactive system (MI2) produced in Examples 72-79 above. The specific dilutions of each and the results attained thereby are presented in Table 7.

TABLE 7

| Example | Dilution Ratio | | T zero | T1.5 OD | T 18 | T68 OD | Delta 68 |
|---|---|---|---|---|---|---|---|
| | Immunox | MI2 | | | | | |
| 96 | | 1:80 | 150 | 152 | | 832 | 682 |
| 97 | | 1:200 | 106 | 112 | | 980 | 874 |
| 98 | 1:64 | | 97 | 107 | 1043 | | |
| 99 | 1:128 | | 111 | 119 | 1126 | | |
| 100 | 1:256 | | 84 | 131 | | 1170 | 1086 |
| 101 | 1:512 | | 81 | 140 | | 1240 | 1159 |
| 102 | 1:256 | 1:80 | 138 | 141 | | 268 | 130 |
| 103 | 1:256 | 1:200 | 102 | 114 | | 1037 | 935 |
| 104 | 1:512 | 1:80 | 138 | 140 | | 292 | 154 |
| 105 | 1:512 | 1:200 | 97 | 110 | | 1031 | 934 |
| 106 | Control 1 | | 86 | 175 | | 754 | 668 |
| 107 | Control 2 | | 87 | 176 | | 1180 | 1093 |

As indicated in Table 7, none of the test vials containing the low levels of each of the bioactive compositions or the Immunox dilution provided antifungal activity through the full 96 hour period tested. Furthermore, neither the 1:128 dilution (Example 99) nor the 1:64 dilution (Example 98) of Immunox provided any measure of efficacy, even in the shorter test period of 18 hours, despite the fact that the manufacturer generally recommends a dilution of 1:64. Similarly, Examples 103 and 105 having a 1:200 dilution of the bioactive composition (~1 ppm of each metal, 0.08% citric acid, 0.00125 NaLS and 0.0016 SLS) in combination with the two dilutions of the Immunox failed to demonstrate bioefficacy whereas combinations of both dilutions of the Immunox with a somewhat higher level, 1:80 dilution, of the bioactive composition (~2.5 ppm of each metal, 0.2% citric acid, 0.003 NaLS and 0.004 SLS) demonstrated bioefficacy. This demonstrates a synergy between the two compositions as the 1:80 dilution by itself failed to show bioefficacy over the full period tested.

Examples 108-126

Metal Sources

A series of experiments were conducted using different metal salts as the metal ion sources. Here, sufficient amounts of silver nitrate, copper sulfate and zinc oxide were added to a 5% aqueous citric acid solution to provide 31.75 ppm silver, 12.5 ppm copper and 40.17 ppm zinc. Different quantities of this stock concentrate solution (MI4) were added to the test vials to assess efficacy. The specific formulations, including the resultant ppm of each metal in the text vial, as well as the results thereof in inhibiting yeast growth were as presented in Tables 8 and 8A.

The results shown in Tables 8 and 8A demonstrate that the selection of the metal ion source is not critical so long as it is readily soluble and is soluble to the extent needed to provide the desired level of metal ion concentration in the solution. Furthermore, the results demonstrate the bioefficacy even at extremely low metal and acid contents. Although, the efficacy is relatively short lived at the lower concentrations, long-term bioefficacy is found with only minor adjustments in the relative concentration of the necessary components. Furthermore, depending upon the ultimate end-use application, such short term antifungal efficacy may be sufficient; thus, enabling one to minimize any environmental contamination from the general application of these materials.

The results also suggest that sodium lauryl sulfate may be ineffective on its own in promoting the bioefficacy of the bioactive compositions of the present invention. Nevertheless, its presence may be desirable where the efficacious surfactant is not readily soluble in the aqueous system. On the other hand, its presence or the presence of like surfactants may not be important where the intent is to produce non-aqueous systems. For example, systems to be applied as an emulsion in water or as an oil that will spread on an aqueous medium to which it is applied, e.g., a rice paddy, may look to surfactants that are less hydrophilic and more lipophilic.

Examples 127-143

Lactic Acid

A series of experiments was conducted similar to the previous with the exception that lactic acid was substituted for citric acid. Hence, the bioactive composition (MI5) comprised sufficient amounts of silver nitrate, copper sulfate and zinc oxide dissolved in a 5% aqueous lactic acid solution to provide 31.75 ppm silver, 12.5 ppm copper and 40.17 ppm zinc. The specific formulations tested and the results attained therewith were as presented in Tables 9 and 9A.

TABLE 8

| Example | Volume MI4 added | Metals Concentration ppm Ag | ppm Cu | ppm Zn | Surfactant (w/w)% NaLS | SDS | Turbidity (NTU) T zero | T 2 | T 18 | T26 | T44 | T48 | T68 |
|---|---|---|---|---|---|---|---|---|---|---|---|---|---|
| 108 | 0.5 | 0.79 | 0.31 | 1.00 | | | 81 | 129 | 950 | 1046 | 1046 | 1046 | 1054 |
| 109 | 1 | 1.59 | 0.63 | 2.01 | | | 85 | 136 | 950 | 997 | 1055 | 990 | 1023 |
| 110 | 2 | 3.18 | 1.25 | 4.02 | | | 112 | 158 | 916 | 930 | 960 | 930 | 970 |
| 111 | 3 | 4.76 | 1.88 | 6.03 | | | 126 | 158 | 760 | 799 | 810 | 830 | 844 |
| 112 | 0.5 | 0.79 | 0.31 | 1.00 | 0.005 | | 140 | 143 | 179 | 307 | 919 | 936 | 980 |
| 113 | 1 | 1.59 | 0.63 | 2.01 | 0.005 | | 140 | 137 | 143 | 152 | 279 | 306 | 458 |
| 114 | 2 | 3.18 | 1.25 | 4.02 | 0.005 | | 180 | 174 | 174 | 177 | 244 | 252 | 282 |
| 115 | 3 | 4.76 | 1.88 | 6.03 | 0.005 | | 187 | 185 | 184 | 184 | 184 | 184 | 272 |
| 116 | 0.5 | 0.79 | 0.31 | 1.00 | | 0.005 | 83 | 132 | 948 | 1054 | 1066 | 1078 | 1097 |
| 117 | 1 | 1.59 | 0.63 | 2.01 | | 0.005 | 97 | 136 | 911 | 1003 | 1100 | 1060 | 1075 |
| 118 | 2 | 3.18 | 1.25 | 4.02 | | 0.005 | 116 | 147 | 748 | 907 | 970 | 1001 | 1006 |
| 119 | 3 | 4.76 | 1.88 | 6.03 | | 0.005 | 124 | 156 | 504 | 701 | 840 | 868 | 916 |
| 120 | 0.5 | 0.79 | 0.31 | 1.00 | 0.0025 | 0.0025 | 140 | 140 | 250 | 640 | 1065 | 1088 | 1133 |
| 121 | 1 | 1.59 | 0.63 | 2.01 | 0.0025 | 0.0025 | 149 | 149 | 160 | 256 | 930 | 901 | 1014 |
| 122 | 2 | 3.18 | 1.25 | 4.02 | 0.0025 | 0.0025 | 154 | 177 | 174 | 174 | 281 | 459 | 804 |
| 123 | 3 | 4.76 | 1.88 | 6.03 | 0.0025 | 0.0025 | 176 | 179 | 177 | 181 | 320 | 445 | 736 |
| 124 | 2 | 3.18 | 1.25 | 4.02 | 0.01 | | 162 | 162 | 162 | 163 | 164 | 164 | 164 |
| 125 | 0.86 | 1.37 | 0.54 | 1.73 | 0.01 | | 150 | 140 | 140 | 140 | 186 | 208 | 254 |
| 126 | | | | | | | 78 | 113 | 877 | 868 | 878 | 865 | 898 |

TABLE 8A

| Example | Volume MI4 added | Metals Concentration ppm Ag | ppm Cu | ppm Zn | Surfactant (w/w)% NaLS | SDS | Change in Turbity (delta NTU) Delta T2-T0 | D T18-T0 | D T26-T0 | D T44-T0 | DT48-T0 | DT68-T0 |
|---|---|---|---|---|---|---|---|---|---|---|---|---|
| 108 | 0.5 | 0.79 | 0.31 | 1.00 | | | 48 | 869 | 965 | 965 | 965 | 973 |
| 109 | 1 | 1.59 | 0.63 | 2.01 | | | 51 | 865 | 912 | 970 | 905 | 938 |
| 110 | 2 | 3.18 | 1.25 | 4.02 | | | 48 | 804 | 818 | 848 | 818 | 858 |
| 111 | 3 | 4.76 | 1.88 | 6.03 | | | 32 | 624 | 673 | 684 | 704 | 718 |
| 112 | 0.5 | 0.79 | 0.31 | 1.00 | 0.005 | | 3 | 39 | 167 | 779 | 796 | 840 |
| 113 | 1 | 1.59 | 0.63 | 2.01 | 0.005 | | −3 | 3 | 12 | 139 | 166 | 328 |
| 114 | 2 | 3.18 | 1.25 | 4.02 | 0.005 | | −8 | −6 | −3 | 64 | 72 | 102 |
| 115 | 3 | 4.76 | 1.88 | 6.03 | 0.005 | | −2 | −3 | −3 | −3 | −3 | 85 |
| 116 | 0.5 | 0.79 | 0.31 | 1.00 | | 0.005 | 49 | 865 | 971 | 983 | 995 | 1014 |
| 117 | 1 | 1.59 | 0.63 | 2.01 | | 0.005 | 39 | 814 | 906 | 1003 | 963 | 978 |
| 118 | 2 | 3.18 | 1.25 | 4.02 | | 0.005 | 31 | 630 | 791 | 854 | 885 | 890 |
| 119 | 3 | 4.76 | 1.88 | 6.03 | | 0.005 | 32 | 380 | 577 | 716 | 744 | 792 |
| 120 | 0.5 | 0.79 | 0.31 | 1.00 | 0.0025 | 0.0025 | 0 | 110 | 500 | 925 | 948 | 993 |
| 121 | 1 | 1.59 | 0.63 | 2.01 | 0.0025 | 0.0025 | 0 | 11 | 107 | 781 | 752 | 865 |
| 122 | 2 | 3.18 | 1.25 | 4.02 | 0.0025 | 0.0025 | 13 | 10 | 10 | 127 | 295 | 640 |
| 123 | 3 | 4.76 | 1.88 | 6.03 | 0.0025 | 0.0025 | 3 | 1 | 5 | 144 | 269 | 560 |
| 124 | 2 | 3.18 | 1.25 | 4.02 | 0.01 | | 0 | 0 | 1 | 1 | 2 | 2 |
| 125 | 0.86 | 1.37 | 0.54 | 1.73 | 0.01 | | −10 | −10 | −10 | 36 | 58 | 104 |
| 126 | | | | | | | 35 | 799 | 788 | 800 | 787 | 820 |

TABLE 9

| Example | Volume MI5 added | Metals Concentration ppm Ag | ppm Cu | ppm Zn | Surfactant (w/w)% NaLS | SDS | Turbidity (NTU) T zero | T1 | T18 | T24 | T44 |
|---|---|---|---|---|---|---|---|---|---|---|---|
| 127 | 0.5 | 0.79 | 0.31 | 1.00 | | | 107 | 130 | 1000 | 1111 | 1001 |
| 128 | 1 | 1.59 | 0.63 | 2.01 | | | 109 | 130 | 1006 | 1021 | 1016 |
| 129 | 2 | 3.18 | 1.25 | 4.02 | | | 148 | 154 | 970 | 995 | 1014 |
| 130 | 3 | 4.76 | 1.88 | 6.03 | | | 178 | 202 | 914 | 925 | 990 |
| 131 | 0.5 | 0.79 | 0.31 | 1.00 | 0.005 | | 134 | 170 | 300 | 454 | 923 |
| 132 | 1 | 1.59 | 0.63 | 2.01 | 0.005 | | 153 | 169 | 200 | 227 | 292 |
| 133 | 2 | 3.18 | 1.25 | 4.02 | 0.005 | | 218 | 217 | 207 | 204 | 228 |
| 134 | 3 | 4.76 | 1.88 | 6.03 | 0.005 | | 222 | 223 | 222 | 215 | 227 |
| 135 | 0.5 | 0.79 | 0.31 | 1.00 | | 0.005 | 120 | 145 | 1074 | 1111 | 1079 |
| 136 | 1 | 1.59 | 0.63 | 2.01 | | 0.005 | 140 | 156 | 1050 | 1092 | 1110 |
| 137 | 2 | 3.18 | 1.25 | 4.02 | | 0.005 | 179 | 193 | 945 | 1031 | 1080 |
| 138 | 3 | 4.76 | 1.88 | 6.03 | | 0.005 | 223 | 239 | 690 | 977 | 1180 |
| 139 | 0.5 | 0.79 | 0.31 | 1.00 | 0.0025 | 0.0025 | 143 | 151 | 884 | 968 | 1170 |
| 140 | 1 | 1.59 | 0.63 | 2.01 | 0.0025 | 0.0025 | 175 | 175 | 237 | 330 | 1110 |
| 141 | 2 | 3.18 | 1.25 | 4.02 | 0.0025 | 0.0025 | 210 | 214 | 207 | 223 | 730 |

TABLE 9-continued

|  | Volume MI5 | Metals Concentration | | | Surfactant (w/w)% | | Turbidity (NTU) | | | | |
|---|---|---|---|---|---|---|---|---|---|---|---|
| Example | added | ppm Ag | ppm Cu | ppm Zn | NaLS | SDS | T zero | T1 | T18 | T24 | T44 |
| 142 | 3 | 4.76 | 1.88 | 6.03 | 0.0025 | 0.0025 | 240 | 240 | 228 | 228 | 475 |
| 143 | control | | | | | | 100 | 139 | 1175 | 1163 | 1170 |

TABLE 9A

|  | Volume MI5 | Metals Concentration | | | Surfactant (w/w)% | | Change in Turbidity (delta NTU) | | | |
|---|---|---|---|---|---|---|---|---|---|---|
| Example | added | ppm Ag | ppm Cu | ppm Zn | NaLS | SDS | D T1-T0 | D T18-T10 | DT24-T0 | DT44-T0 |
| 127 | 0.5 | 0.79 | 0.31 | 1.00 | | | 23 | 893 | 1004 | 894 |
| 128 | 1 | 1.59 | 0.63 | 2.01 | | | 21 | 897 | 912 | 907 |
| 129 | 2 | 3.18 | 1.25 | 4.02 | | | 8 | 822 | 847 | 866 |
| 130 | 3 | 4.76 | 1.88 | 6.03 | | | 24 | 736 | 747 | 812 |
| 131 | 0.5 | 0.79 | 0.31 | 1.00 | 0.005 | | 36 | 166 | 320 | 789 |
| 132 | 1 | 1.59 | 0.63 | 2.01 | 0.005 | | 16 | 47 | 74 | 139 |
| 133 | 2 | 3.18 | 1.25 | 4.02 | 0.005 | | −1 | −11 | −14 | 10 |
| 134 | 3 | 4.76 | 1.88 | 6.03 | 0.005 | | 1 | 0 | −7 | 5 |
| 135 | 0.5 | 0.79 | 0.31 | 1.00 | | 0.005 | 25 | 954 | 991 | 959 |
| 136 | 1 | 1.59 | 0.63 | 2.01 | | 0.005 | 16 | 910 | 952 | 970 |
| 137 | 2 | 3.18 | 1.25 | 4.02 | | 0.005 | 14 | 766 | 852 | 901 |
| 138 | 3 | 4.76 | 1.88 | 6.03 | | 0.005 | 16 | 467 | 754 | 957 |
| 139 | 0.5 | 0.79 | 0.31 | 1.00 | 0.0025 | 0.0025 | 8 | 741 | 825 | 1027 |
| 140 | 1 | 1.59 | 0.63 | 2.01 | 0.0025 | 0.0025 | 0 | 62 | 155 | 935 |
| 141 | 2 | 3.18 | 1.25 | 4.02 | 0.0025 | 0.0025 | 4 | −3 | 13 | 520 |
| 142 | 3 | 4.76 | 1.88 | 6.03 | 0.0025 | 0.0025 | 0 | −12 | −12 | 235 |
| 143 | control | | | | | | 39 | 1075 | 1063 | 1070 |

The results as shown in Tables 9 and 9A, mimic those found in the previous set of experiments indicating that the invention is translatable to acids of similar characteristics.

Examples 144-156

Phosphoric Acid

Two stock solutions were prepared for evaluation wherein the acid employed was phosphoric acid. In the first, silver citrate, copper citrate and zinc citrate were added to a 16% aqueous phosphoric acid solution to provide 200 ppm of each metal. A second stock solution was prepared using silver nitrate, copper sulfate and zinc oxide, again in the 16% phosphoric acid solution to provide 200 ppm of each metal. Both composition further contained 0.32% surfactant, either as an individual surfactant or as a 50:50 mix. The specific formulations and the results of their efficacy in controlling yeast growth were as presented in Tables 10 and 10A.

The results as shown in Tables 10 and 10A suggest that the surfactant may not be critical in those compositions wherein the excess acid is a strong to moderate acid, such as phosphoric acid.

Examples 157-166

Nitric Acid

To further demonstrate the breadth of the bioactive compositions, a relatively strong mineral acid, nitric acid, was employed as the acid component. A stock solution was prepared by combining 78.7 mg silver nitrate, 62.2 mg zinc oxide and 200 mg copper sulfate with 20 ml of purified water and 1.5 g concentrated nitric acid (68%) under constant agitation. Once the solids were dissolved, additional purified water was added to make up a 250 volume. As prepared, this mixture contained approximately 200 ppm of each metal, as calculated. The pH was measured and found to be 1.66. The mixture was then divided into three aliquots of approximately equal volume. One aliquot was set aside and the other two were subjected to pH adjustment with ammonia hydroxide. The amount of ammonia hydroxide was added was that necessary to bring the pH of the first aliquot up to 2.55 and the second aliquot up to 3.63.

Each solution was then evaluated, with and without surfactants, to assess their bioefficacy in inhibiting the growth of yeast. The amount of each of the three aliquots added to the 20 ml vial of the yeast suspension is set forth in

TABLE 10

|  |  |  |  | Turbidity (NTU | | | | | | | |
|---|---|---|---|---|---|---|---|---|---|---|---|
| Example | Metal source | Metal (ppm) | Surfactants (w/w) | T zero | T 1 hour | T 18 | T 24 | T 42 | T48 | T72 | T 96 |
| 144 | Citrate salts* | 2.5 | | 123 | 134 | 300 | 400 | 1046 | 1094 | 1146 | 1106 |
| 145 | Citrate salts* | 5 | | 199 | 180 | 166 | 166 | 160 | 163 | 162 | 154 |
| 146 | Citrate salts* | 10 | | 211 | 193 | 176 | 176 | 172 | 177 | 172 | 169 |
| 147 | AgNO3, CuSO4, ZnO | 2.5 | | 168 | 166 | 179 | 179 | 172 | 174 | 778 | 1162 |
| 148 | AgNO3, CuSO4, ZnO | 5 | | 209 | 193 | 180 | 180 | 175 | 174 | 170 | 168 |
| 149 | AgNO3, CuSO4, ZnO | 10 | | 228 | 219 | 197 | 197 | 196 | 204 | 199 | 194 |

TABLE 10-continued

| | | | | Turbidity (NTU) | | | | | | | |
|---|---|---|---|---|---|---|---|---|---|---|---|
| Example | Metal source | Metal (ppm) | Surfactants (w/w) | T zero | T 1 hour | T 18 | T 24 | T 42 | T 48 | T 72 | T 96 |
| 150 | Citrate salts* | 5 | 0.05 SLS | 226 | 218 | 200 | 200 | 193 | 203 | 192 | 186 |
| 151 | Citrate salts* | 5 | 0.05 NaLS | 258 | 254 | 216 | 216 | 200 | 205 | 197 | 185 |
| 152 | Citrate salts* | 5 | 0.05 SLS/0.05 NaLS | 253 | 237 | 200 | 200 | 204 | 208 | 201 | 188 |
| 153 | AgNO3, CuSO4, ZnO | 5 | 0.05 SLS | 285 | 263 | 229 | 229 | 223 | 229 | 214 | 206 |
| 154 | AgNO3, CuSO4, ZnO | 5 | 0.05 NaLS | 280 | 273 | 226 | 222 | 216 | 213 | 208 | 184 |
| 155 | AgNO3, CuSO4, ZnO | 5 | 0.05 SLS/0.05 NaLS | 283 | 272 | 250 | 247 | 232 | 238 | 232 | 215 |
| 156 | Control | | | 52 | 53 | 437 | 599 | 938 | 913 | 877 | 886 |

*Ag citrate, Cu citrate and Zn citrate, each at level designated

TABLE 10A

| | | | | Change in Turbidity (delta NTU) | | | | | | |
|---|---|---|---|---|---|---|---|---|---|---|
| Example | Metal source | Metal (ppm) | Surfactants (w/w) | T1-T0 | T18-T1 | T24-T1 | T42-T1 | T48-T1 | T72-T1 | T 96-T 1 |
| 144 | Citrate salts* | 2.5 | | 11 | 166 | 266 | 912 | 960 | 1012 | 972 |
| 145 | Citrate salts* | 5 | | −19 | −14 | −14 | −20 | −17 | −18 | −26 |
| 146 | Citrate salts* | 10 | | −18 | −17 | −17 | −21 | −16 | −21 | −24 |
| 147 | AgNO3, CuSO4, ZnO | 2.5 | | −2 | 13 | 13 | 6 | 8 | 612 | 996 |
| 148 | AgNO3, CuSO4, ZnO | 5 | | −16 | −13 | −13 | −18 | −19 | −23 | −25 |
| 149 | AgNO3, CuSO4, ZnO | 10 | | −9 | −22 | −22 | −23 | −15 | −20 | −25 |
| 150 | Citrate salts* | 5 | 0.05 SLS | −8 | −18 | −18 | −25 | −15 | −26 | −32 |
| 151 | Citrate salts* | 5 | 0.05 NaLS | −4 | −38 | −38 | −54 | −49 | −57 | −69 |
| 152 | Citrate salts* | 5 | 0.05 SLS/0.05 NaLS | −16 | −37 | −37 | −33 | −29 | −36 | −49 |
| 153 | AgNO3, CuSO4, ZnO | 5 | 0.05 SLS | −22 | −34 | −34 | −40 | −34 | −49 | −57 |
| 154 | AgNO3, CuSO4, ZnO | 5 | 0.05 NaLS | −7 | −47 | −51 | −57 | −60 | −65 | −89 |
| 155 | AgNO3, CuSO4, ZnO | 5 | 0.05 SLS/0.05 NaLS | −11 | −22 | −25 | −40 | −34 | −40 | −57 |
| 156 | Control | | | 1 | 384 | 546 | 885 | 860 | 824 | 833 |

Table 11 together with the amount of surfactant added, where indicated. The surfactant employed was a 50:50 mix of sodium lauryl sulfate and sodium lauroyl sarcosinate. The specific formulations tested and the results thereof are presented in Table 11. As can be seen from Table 11, the combination of metal and acid did not provide any inhibition at the levels tested. However, when the surfactant was added, bio-efficacy was manifested even at the lower metal/acid concentration.

TABLE 11

| | | | Nitric Acid | | | | | |
|---|---|---|---|---|---|---|---|---|
| | Vol. MI6 | Metals | Surfactant | | | Turbidity/Change in Turbidity | | |
| Example | Added | (ppm) | (w/w)% | pH | T0 | T18 | T18-T0 | T42 | T42-T0 |
| 157 | 0.5 | 5 | | 1.66 | 69 | 1243 | 1174 | 1133 | 1064 |
| 158 | 0.5 | 5 | | 2.55 | 67 | 1245 | 1178 | 1133 | 1066 |
| 159 | 0.5 | 5 | | 3.63 | 69 | 1243 | 1174 | 1150 | 1081 |
| 160 | 1 | 10 | | 1.66 | 65 | 976 | 911 | 1162 | 1097 |
| 161 | 1 | 10 | | 2.55 | 66 | 1012 | 946 | 1186 | 1120 |
| 162 | 1 | 10 | | 3.63 | 67 | 1036 | 969 | 1166 | 1099 |
| 163 | 0.5 | 5 | 0.05 | 1.66 | 61 | 55 | −6 | 58 | −3 |
| 164 | 0.5 | 5 | 0.05 | 2.55 | 62 | 53 | −9 | 55 | −7 |
| 165 | 0.5 | 5 | 0.05 | 3.63 | 60 | 57 | −3 | 52 | −8 |
| 166 | 0 | | | | 67 | 1255 | 1188 | 1212 | 1145 |

Examples 167-222

Surfactant Evaluation

A series of experiments were conducted to screen various surfactants for efficacy in accordance with the present invention. The surfactants were evaluated as a neat additive (0 ppm metals) or in combination with either 1 ml or 2 ml of a 4% citric acid solution containing 50 ppm each of copper, silver and zinc. With the addition of 1 ml of the citric acid solution, the test vial of the yeast suspension will have about 0.2% citric acid and about 2.5 ppm of each metal. With the addition of 2 ml of the citric acid solution, the acid is approximately 0.4% and the metals are each present at about 5 ppm in the test vials. Each surfactant was evaluated at a concentration of approximately 0.05 wt %. Controls were also evaluated with and without the metals.

The specific surfactants evaluated as well as the formulations of each test composition together with the results thereof are set forth in Table 12. As

TABLE 12

| Surfactants | Surfactant Chemistry | Source | Type | Metal ppm | T0 | T18 | T48 | T72 | T96 | T18-T0 | T48-T0 | T72-T0 | T96-T0 |
|---|---|---|---|---|---|---|---|---|---|---|---|---|---|
| Pluronic L62 | EO-PO Block copolymer | BASF | Non-ionic | 0 | 47 | 1088 | 1113 | 1142 | 1156 | 1041 | 1066 | 1095 | 1109 |
| | | | | 2.5 | 343 | 376 | 382 | 364 | 340 | 33 | 19 | 2 | −24 |
| | | | | 5 | 118 | 1127 | 1138 | 1175 | 1146 | 1009 | 1020 | 1057 | 1028 |
| Hampopsyl L95 | Na N-lauroyl Sarcosinate | Hampshire Chemical | An-ionic | 0 | 47 | 42 | 390 | 884 | 878 | −5 | 343 | 837 | 831 |
| | | | | 2.5 | 70 | 909 | 999 | 1037 | 983 | 839 | 929 | 957 | 913 |
| | | | | 5 | 407 | 444 | 442 | 440 | 440 | 37 | 35 | 33 | 33 |
| Sodium Lauryl Sulfate | Sodium Lauryl Sulfate | VWR Scientific | An-ionic | 0 | 48 | 495 | 658 | 642 | 839 | 447 | 610 | 694 | 591 |
| | | | | 2.5 | 88 | 90 | 88 | 88 | 87 | 2 | 0 | 0 | −1 |
| | | | | 5 | 231 | 244 | 233 | 238 | 232 | 13 | 2 | 7 | 1 |
| Witco | Sodium Laurylether Sulfate (2 mole EO) | Witco Chemical | An-ionic | 0 | 48 | 1060 | 1021 | 957 | 923 | 1012 | 973 | 903 | 875 |
| | | | | 2.5 | 73 | 819 | 1415 | 1436 | 1447 | 746 | 1342 | 1363 | 1374 |
| | | | | 5 | 140 | 143 | 446 | 870 | 915 | 3 | 306 | 730 | 775 |
| Jeenteric CAPB LC | Cocamidopropyl betaine | Jeen International Corp | Ampho-teric | 0 | 48 | 845 | 657 | 882 | 462 | 597 | 609 | 834 | 414 |
| | | | | 2.5 | 93 | 90 | 91 | 90 | 88 | −3 | −2 | −3 | −5 |
| | | | | 5 | 204 | 204 | 202 | 202 | 202 | 0 | −2 | −2 | −2 |
| Manckinate LO100 DLSS | Dilauryl sulfosuccinate | Mackintire Chemical | ampho-teric | 0 | 95 | 1020 | 866 | 817 | 788 | 925 | 771 | 722 | 693 |
| | | | | 2.5 | 118 | 97 | 106 | 1165 | 1317 | −21 | −12 | 1047 | 1189 |
| | | | | 5 | 251 | 239 | 232 | 224 | 215 | −12 | −19 | −27 | −36 |
| Ammonyx LO | Lauryl Dimethyamine Oxide | Stepan Chemical | Non-ionic | 0 | 44 | 28 | 35 | 45 | 28 | −16 | −9 | 1 | −18 |
| | | | | 2.5 | 972 | 390 | 118 | 115 | 105 | −582 | −854 | −857 | −867 |
| | | | | 5 | 652 | 314 | 252 | 227 | 180 | −338 | −400 | −425 | −472 |
| Hamposyl C30 | Na N-cocoyl Sarcosinate | Hampshire Chemical | An-ionic | 0 | 44 | 207 | 1043 | 1041 | 1037 | 163 | 999 | 997 | 993 |
| | | | | 2.5 | 699 | 677 | 657 | 673 | 1115 | −22 | −42 | −26 | 416 |
| | | | | 5 | 510 | 554 | 576 | 589 | 593 | 44 | 88 | 78 | 83 |
| Hamposyl M30 | Na N-myristoyl Sarcosinate | Hampshire Chemical | An-ionic | 0 | 46 | 28 | 152 | 1205 | 1184 | −18 | 106 | 1159 | 1138 |
| | | | | 2.5 | 588 | 564 | 1372 | 1385 | 1389 | −24 | 754 | 797 | 801 |
| | | | | 5 | 583 | 586 | 1299 | 1382 | 1383 | 3 | 718 | 799 | 800 |
| Hampshire TL Glutamate | TEA lauroyl Glutamate | Hampshire Chemical | An-ionic | 0 | 86 | 946 | 977 | 927 | 905 | 880 | 811 | 861 | 839 |
| | | | | 2.5 | 182 | 410 | 1143 | 1189 | 1178 | 228 | 951 | 1007 | 996 |
| | | | | 5 | 218 | 618 | 1104 | 1129 | 1162 | 400 | 856 | 911 | 944 |
| Tergitol 15S3 | Secondary Alcohol Ethoxylate | Dow Chemical | Non-ionic | 0 | 185 | 1140 | 1178 | 969 | 880 | 952 | 990 | 781 | 892 |
| | | | | 2.5 | 180 | 340 | 1247 | 1227 | 1134 | 180 | 1067 | 1047 | 954 |
| | | | | 5 | 317 | 818 | 1350 | 1297 | 1289 | 501 | 1033 | 980 | 972 |
| Tergitol 15S7 | Secondary Alcohol Ethoxylate | Dow Chemical | Non-ionic | 0 | 48 | 865 | 1077 | 766 | 577 | 817 | 1029 | 718 | 529 |
| | | | | 2.5 | 91 | 117 | 1152 | 1087 | 917 | 26 | 1061 | 996 | 828 |
| | | | | 5 | 197 | 408 | 1291 | 1224 | 1217 | 211 | 1094 | 1027 | 1020 |
| Tergitol TMN6 | Branched Secondary Alcohol Ethoxylate | Dow Chemical | Non-ionic | 0 | 50 | 940 | 1128 | 784 | 614 | 890 | 1078 | 734 | 584 |
| | | | | 2.5 | 106 | 132 | 1184 | 1140 | 1048 | 26 | 1078 | 1034 | 942 |
| | | | | 5 | 215 | 480 | 1000 | 1275 | 1266 | 285 | 1085 | 1060 | 1051 |
| Tergitol TMN3 | Branched Secondary Alcohol Ethoxylate | Dow Chemical | Non-ionic | 0 | 49 | 314 | 1015 | 700 | 541 | 285 | 966 | 651 | 492 |
| | | | | 2.5 | 92 | 94 | 1054 | 1014 | 878 | 2 | 962 | 922 | 784 |
| | | | | 5 | 189 | 247 | 1100 | 1128 | 1128 | 58 | 911 | 939 | 939 |
| Sulfonic TDA3B | C1-C14 Ethoxylated Alcohol | Huntsmen Chemical | Non-ionic | 0 | 206 | 1163 | 1183 | 948 | 809 | 957 | 977 | 742 | 603 |
| | | | | 2.5 | 280 | 372 | 1296 | 1248 | 1192 | 112 | 1038 | 888 | 932 |
| | | | | 5 | 359 | 725 | 1389 | 1368 | 1319 | 388 | 1010 | 1007 | 960 |
| Tween 20 | polyoxyethylene (20) sorbitan monolaurate | | Non-ionic | 0 | 57 | 1077 | 1118 | 1087 | 730 | 1020 | 1061 | 1030 | 673 |
| | | | | 2.5 | 92 | 932 | 1116 | 867 | 719 | 840 | 1024 | 775 | 627 |
| | | | | 5 | 189 | 1080 | 1144 | 1105 | 1048 | 911 | 975 | 938 | 879 |
| Plantaren 2000 | Alkyl polyglycoside | Cognis | Non-ionic | 0 | 56 | 345 | 905 | 782 | 642 | 290 | 850 | 726 | 586 |
| | | | | 2.5 | 102 | 410 | 660 | 1104 | 1323 | 308 | 558 | 1002 | 1221 |
| | | | | 5 | 229 | 235 | 232 | 232 | 237 | 8 | 3 | 3 | 8 |
| Control | | | | 0 | 58 | 1171 | 1152 | 1168 | 1177 | 1113 | 1094 | 1110 | 1119 |
| Control (2.5 ppm) | | | | 0 | 94 | 965 | 1073 | 1180 | 1041 | 874 | 979 | 1058 | 947 |
| Control (5 ppm) | | | | 0 | 132 | 1196 | 1185 | 1228 | 1233 | 1064 | 1053 | 1096 | 1101 |
| Metals Control | | | | 2.5 | 93 | 1001 | 1080 | 1128 | 962 | 908 | 987 | 1035 | 889 |
| Metals Control | | | | 5 | 152 | 1160 | 1185 | 1228 | 1193 | 1008 | 1034 | 1076 | 1041 | seen in Table 12, the benefits of the present invention are realized with a broad array of surfactant materials. Especially preferred surfactants are those that are free or substantially free of repeat ethylene oxide units and/or have moderate to lower molecular weights. Despite the foregoing, it is noted that good results were attained with the Pluronic L62, a polyethylene oxide containing surfactant, when used in combination with the lower level of acid and metals. It is thought that the higher acid level may have affected the stability of this material, and possibly like materials.

Examples 223-236

Strobilurin Comparison

A series of experiments were conducted in order to evaluate the comparative performance of the bioactive compositions of the present invention and several commercial strobilurin based fungicides. Two bioactive formulations were used. The first, MI2, comprised a 16% aqueous citric acid solution having dissolved therein silver citrate, copper citrate and zinc citrate, each being added in an amount to provide 200 ppm of each metal, together with 0.25% sodium Lauroyl sarcosinate and 0.32% sodium lauryl sulfate, as noted above. The second, MI7, comprised a 160:1 dilution of a 16% aqueous phosphoric acid solution having dissolved therein silver citrate, copper citrate and zinc citrate, each being added in an amount to provide 200 ppm of each metal in the phosphoric acid solution. Each fungicide was evaluated at different levels. The specific formulations tested and the results attained therewith are presented in Tables 13 and 13A.

As seen in Tables 13 and 13A, the bioactive compositions of the present invention provided marked inhibition of yeast growth, even at the lower concentrations, ~5 ppm of each metal ion. On the other hand, all but two of the strobilurin based fungicide formulations tested failed to demonstrate any significant bioefficacy against yeast over the time period tested. The two formulations that provided good inhibition were at comparatively high loadings.

Examples 237-250

Strobilurin Synergy

In light of the foregoing poor performance of the strobilurins generally, a series of experiments were conducted in order to evaluate the potential synergy between the bioactive compositions of the present invention and the foregoing commercial strobilurin based fungicides. The compositions employed were the

TABLE 13

| | | | Turbidity (NTU) | | | | |
|---|---|---|---|---|---|---|---|
| Example | Fungicide | vol. Added | T0 | T1 | T18 | T26 | T50 |
| 223 | Quadris[a] | 1 | 384 | 393 | 1066 | 1139 | 1134 |
| 224 | | 2 | 767 | 772 | 1264 | 1311 | 1315 |
| 225 | | 5 | 1332 | 1332 | 1364 | 1377 | 1376 |
| 226 | Flint[b] | 1 | 418 | 424 | 1115 | 1208 | 1234 |
| 227 | | 2 | 718 | 708 | 1141 | 1299 | 1327 |
| 228 | | 5 | 1210 | 1210 | 1270 | 1265 | 1245 |
| 229 | Headline[c] | 1 | 232 | 225 | 961 | 1114 | 1137 |
| 230 | | 2 | 387 | 391 | 1066 | 1134 | 1199 |
| 231 | | 5 | 717 | 747 | 1178 | 1222 | 1241 |
| 232 | MI2 | 0.5 | 128 | 129 | 154 | 177 | 174 |
| 233 | MI2 | 1 | 414 | 384 | 366 | 366 | 352 |
| 234 | MI7 | 0.5 | 249 | 244 | 248 | 248 | 242 |
| 235 | MI7 | 1 | 311 | 302 | 283 | 283 | 277 |
| 236 | Control | | 67 | 68 | 793 | 871 | 904 |

[a]Quadris fungicide from Syngenta Crop Protections, Inc. of Greensboro, NC, USA
[b]Flint fungicide from Bayer CropScience LP of Research Triangle Park, NC, USA
[c]Headline from BASF Corporation of Research Triangle Park, NC, USA

TABLE 13A

| | | | Change in Turbidity (delta NTU) | | |
|---|---|---|---|---|---|
| Example | Fungicide | vol. Added | T18-T1 | T26-T1 | T50-T1 |
| 223 | Quadris[a] | 1 | 673 | 746 | 741 |
| 224 | | 2 | 492 | 539 | 543 |
| 225 | | 5 | 32 | 45 | 44 |
| 226 | Flint[b] | 1 | 691 | 784 | 810 |
| 227 | | 2 | 433 | 591 | 619 |
| 228 | | 5 | 60 | 55 | 35 |
| 229 | Headline[c] | 1 | 736 | 889 | 912 |
| 230 | | 2 | 675 | 743 | 808 |
| 231 | | 5 | 431 | 475 | 494 |
| 232 | MI2 | 0.5 | 25 | 48 | 45 |
| 233 | MI2 | 1 | −18 | −18 | −32 |
| 234 | MI7 | 0.5 | 4 | 4 | −2 |
| 235 | MI7 | 1 | −19 | −19 | −25 |
| 236 | Control | | 725 | 803 | 836 |

[a]Quadris fungicide from Syngenta Crop Protections, Inc. of Greensboro, NC, USA
[b]Flint fungicide from Bayer CropScience LP of Research Triangle Park, NC, USA
[c]Headline from BASF Corporation of Research Triangle Park, NC, USA

TABLE 14

| | | | | | Turbidity (NTU) | | | | |
|---|---|---|---|---|---|---|---|---|---|
| Example | Bioactive | Vol. Added | Fungicide[a] | Vol. Added | T0 | T1 | T18 | T24 | T96 |
| 237 | MI2 | 0.25 | Q | 1 | 552 | 554 | 544 | 670 | 1315 |
| 238 | MI2 | 0.25 | Q | 2 | 896 | 894 | 868 | 891 | 1470 |
| 239 | MI2 | 0.5 | Q | 1 | 588 | 578 | 564 | 564 | 608 |
| 240 | MI2 | 0.25 | F | 1 | 578 | 599 | 568 | 568 | 1320 |
| 241 | MI2 | 0.25 | F | 2 | 900 | 900 | 886 | 886 | 1330 |
| 242 | MI2 | 0.25 | H | 1 | 436 | 433 | 454 | 454 | 1312 |
| 243 | MI2 | 0.25 | H | 2 | 611 | 637 | 667 | 632 | 1302 |
| 244 | MI7 | 0.25 | Q | 1 | 558 | 574 | 640 | 668 | 1273 |
| 245 | MI7 | 0.25 | F | 1 | 517 | 560 | 990 | 1197 | 1396 |
| 246 | MI7 | 0.25 | H | 1 | 465 | 476 | 605 | 587 | 1290 |
| 247 | Control | | — | | 93 | 101 | 901 | 986 | 1075 |
| 248 | MI2 | 0.5 | | | 499 | 440 | 390 | 390 | 373 |
| 249 | MI2 | 0.25 | | | 182 | 179 | 175 | 176 | 1122 |
| 250 | MI2 | 0.5 | | | 262 | 260 | 260 | 275 | 275 |

[a]Q—Quadris fungicide from Syngenta Crop Protections, Inc. of Greensboro, NC, USA; F—Flint fungicide from Bayer CropScience LP of Research Triangle Park, NC, USA; and H—Headline from BASF Corporation of Research Triangle Park, NC, USA

TABLE 14A

| Example | Bioactive | Vol. Added | Fungicide[a] | Vol. Added | Change in Turbidity (delta NTU) T18-T1 | T24-T1 | T96-T1 |
|---|---|---|---|---|---|---|---|
| 237 | MI2 | 0.25 | Q | 1 | −10 | 116 | 761 |
| 238 | MI2 | 0.25 | Q | 2 | −26 | −3 | 576 |
| 239 | MI2 | 0.5 | Q | 1 | −14 | −14 | 30 |
| 240 | MI2 | 0.25 | F | 1 | −31 | −31 | 721 |
| 241 | MI2 | 0.25 | F | 2 | −14 | −14 | 430 |
| 242 | MI2 | 0.25 | H | 1 | 21 | 21 | 879 |
| 243 | MI2 | 0.25 | H | 2 | 30 | −5 | 665 |
| 244 | MI7 | 0.25 | Q | 1 | 66 | 94 | 699 |
| 245 | MI7 | 0.25 | F | 1 | 430 | 637 | 836 |
| 246 | MI7 | 0.25 | H | 1 | 129 | 111 | 814 |
| 247 | Control | | — | | 800 | 885 | 974 |
| 248 | MI2 | 0.5 | | | −50 | −50 | −67 |
| 249 | MI2 | 0.25 | | | −4 | −3 | 943 |
| 250 | MI2 | 0.5 | | | 0 | 15 | 15 |

[a]Q—Quadris fungicide from Syngenta Crop Protections, Inc. of Greensboro. NC, USA; F—Flint fungicide from Bayer CropScience LP of Research Triangle Park, NC, USA; and H—Headline from BASF Corporation of Research Triangle Park, NC, USA same as used in the previous set of examples. The specific formulations tested and the results attained therewith are presented in Tables 14 and 14A.

As seen in Tables 14 and 14A, the combination of the bioactive compositions of the present invention with the strobilurin products produced a synergy whereby even the lowest levels of the strobilurin products tested produced a significant inhibition in yeast growth, even though these products appear to increase yeast growth when used alone, as shown in the Tables 13 and 13A.

Examples 251-259

Copper/Zinc Study

A series of experiments were conducted to demonstrate the bioefficacy of binary metal systems as compared to the ternary system used in most other examples. Here a solution of MI2 was compared to a similar composition containing 300 ppm of copper and 300 ppm of zinc (i.e., a 16% aqueous citric acid solution having dissolved therein copper citrate and zinc citrate, each being added in an amount to provide 300 ppm of each metal, together with 0.25% sodium Lauroyl sarcosinate and 0.32% sodium lauryl sulfate). The two bioactive compositions were evaluated at different loadings to assess their bioefficacy. The specific formulations tested and the results attained therewith are presented in Tables 15 and 15A.

As seen in Tables 15 and 15A, both the binary (copper/zinc—Cu/Zn) and the MI2 ternary silver/copper/zinc antimicrobial bioactive compositions demonstrated comparable bioefficacy in inhibiting the growth of yeast.

TABLE 15

| | Composition (gm) | | | | | | |
|---|---|---|---|---|---|---|---|
| Example | Cu/Zn | MI2 | T0 | T1 | T18 | T24 | T46 |
| 251 | 1 | | 776 | 586 | 468 | 463 | 436 |
| 252 | 0.5 | | 292 | 269 | 250 | 250 | 245 |
| 253 | 0.2 | | 147 | 162 | 772 | 1055 | 1075 |
| 254 | 0.1 | | 93 | 125 | 1076 | 1070 | 1036 |
| 255 | Control | | 66 | 127 | 1020 | 1012 | 1137 |
| 256 | | 1 | 830 | 633 | 547 | 522 | 500 |
| 257 | | 0.5 | 335 | 320 | 292 | 302 | 284 |
| 258 | | 0.2 | 152 | 178 | 512 | 1064 | 1098 |
| 259 | | 0.1 | 90 | 136 | 1083 | 1087 | 1067 |

TABLE 15A

| | Composition (gm) | | T1-T0 | T18-T0 | T24-T0 | T46-T0 |
|---|---|---|---|---|---|---|
| | Cu/Zn | MI2 | | | | |
| 251 | 1 | | −190 | −118 | −5 | −27 |
| 252 | 0.5 | | −23 | −19 | 0 | −5 |
| 253 | 0.2 | | 15 | 610 | 283 | 20 |
| 254 | 0.1 | | 32 | 951 | −6 | −34 |
| 255 | Control | | 61 | 893 | −8 | 125 |
| 256 | | 1 | −197 | −86 | −25 | −22 |
| 257 | | 0.5 | −15 | −28 | 10 | −18 |
| 258 | | 0.2 | 26 | 334 | 552 | 34 |
| 259 | | 0.1 | 46 | 947 | 4 | −20 |

Examples 260-269

Mancozeb Synergy

A further series of experiments were conducted to assess the bioefficacy, especially the synergy, of the bioactive agrichemical composition containing Mancozeb (an ethylene bisdithiocarbamate) and the MI2 bioactive acid solution (MI2). The specific formulations tested and the results attained therewith are presented in Table 16 and 16A.

TABLE 16

| | Composition (gm) | | | | | | |
|---|---|---|---|---|---|---|---|
| Example | Mancozeb | MI2 | T0 | T2 | T18 | T24 | T44 |
| 260 | 0.5 | | 934 | 976 | 1220 | 1095 | 1091 |
| 261 | 0.4 | | 780 | 859 | 1021 | 982 | 1052 |
| 262 | 0.3 | | 624 | 717 | 1209 | 1067 | 1113 |
| 263 | 0.2 | | 392 | 489 | 1035 | 933 | 1073 |
| 264 | | 0.2 | 57 | 55 | 54 | 72 | 756 |
| 265 | 0.5 | 0.2 | 930 | 897 | 864 | 839 | 788 |
| 266 | 0.4 | 0.2 | 727 | 709 | 684 | 664 | 591 |
| 267 | 0.3 | 0.2 | 537 | 555 | 535 | 509 | 460 |
| 268 | 0.2 | 0.2 | 370 | 369 | 370 | 343 | 331 |
| 269 | Control | | 23 | 106 | 935 | 824 | 917 |

TABLE 16A

| Example | Composition (gm) Mancozeb | MI2 | T2-T0 | T18-T0 | T24-T0 | T44-T0 |
|---|---|---|---|---|---|---|
| 260 | 0.5 | | 42 | 286 | 161 | 157 |
| 261 | 0.4 | | 79 | 241 | 202 | 272 |
| 262 | 0.3 | | 93 | 585 | 443 | 489 |
| 263 | 0.2 | | 97 | 643 | 541 | 681 |
| 264 | | 0.2 | −2 | −3 | 15 | 699 |
| 265 | 0.5 | 0.2 | −33 | −66 | −91 | −142 |
| 266 | 0.4 | 0.2 | −18 | −43 | −63 | −136 |

TABLE 16A-continued

| Example | Composition (gm) Mancozeb | MI2 | T2-T0 | T18-T0 | T24-T0 | T44-T0 |
|---|---|---|---|---|---|---|
| 267 | 0.3 | 0.2 | 18 | −2 | −28 | −77 |
| 268 | 0.2 | 0.2 | −1 | 0 | −27 | −39 |
| 269 | Control | | 83 | 912 | 801 | 894 |

As seen in Tables 16 and 16A, the mancozeb by itself was ineffective at all levels tested. The bioactive acid solution by itself provided modest bioefficacy, in spite of the very low level of antimicrobial metal ions; however, the suitable bioefficacy appeared to have been lost after 44 hours. In sharp contrast, the combination of the two, at all levels of the mancozeb, demonstrated excellent bioefficacy, even after 44 hours.

Examples 270-293

Amine Oxide Surfactant Study

A series of experiments were conducted to demonstrate the bioefficacy of amine oxide surfactants, specifically, lauryl dimethyl amine oxide (LDAO), alone and in combination with sodium lauroyl sarcosinate (NaLS) and/or sodium lauryl sulfate (SLS). In this instance a very dilute antimicrobial metal-acid solution was employed: 0.08% citric acid and 1 ppm each of silver, copper and zinc. The surfactants were employed at different levels to assess the lowest concentration at which synergy is realized. The specific formulations tested and the results attained therewith are presented in Table 17.

As seen in Table 17, even at such low concentration of acid and metal, the addition of only 0.0025% lauryl dimethyl amine oxide surfactant showed bioefficacy, with modest bioefficacy at the 0.00125% level with sodium lauroyl sarcosinate or the combination of sodium lauroyl sarcosinate and/or sodium lauryl sulfate. At 0.0025% lauryl dimethyl amine oxide, marked bioefficacy

TABLE 17

| Example | LDAO (w/w)% | NaLS (w/w)% | SLS (w/w)% | AG, Cu, Zn ppm | T zero | T 1 | T42 | T66 | T42-T1 | T66-T1 |
|---|---|---|---|---|---|---|---|---|---|---|
| 270 | 0.00025 | | | | 132 | 219 | 1145 | 1133 | 926 | 914 |
| 271 | 0.00125 | | | | 141 | 211 | 1120 | 1039 | 909 | 828 |
| 272 | 0.0025 | | | | 161 | 196 | 862 | 814 | 666 | 618 |
| 273 | 0.00025 | | | 1 | 142 | 209 | 1108 | 1138 | 899 | 929 |
| 274 | 0.00125 | | | 1 | 144 | 208 | 1080 | 1076 | 872 | 868 |
| 275 | 0.0025 | | | 1 | 156 | 208 | 963 | 969 | 755 | 761 |
| 276 | | | | | 144 | 239 | 1232 | 1216 | 993 | 977 |
| 277 | 0.00025 | 0.00025 | | | 144 | 217 | 1084 | 1042 | 867 | 825 |
| 278 | 0.00125 | 0.00125 | | | 136 | 169 | 860 | 784 | 691 | 615 |
| 279 | 0.0025 | 0.0025 | | | 136 | 136 | 562 | 543 | 426 | 407 |
| 280 | 0.00025 | 0.00025 | | 1 | 150 | 216 | 1032 | 1021 | 816 | 805 |
| 281 | 0.00125 | 0.00125 | | 1 | 165 | 186 | 872 | 852 | 686 | 666 |
| 282 | 0.0025 | 0.0025 | | 1 | 174 | 184 | 295 | −3 | 111 | |
| 283 | | 0.00025 | | | 149 | 248 | 1138 | 1165 | 890 | 917 |
| 284 | | 0.00125 | | | 142 | 202 | 1019 | 1018 | 817 | 816 |
| 285 | | 0.0025 | | | 147 | 207 | 1034 | 1007 | 827 | 800 |
| 286 | | | | 1 | 153 | 242 | 1167 | 1178 | 925 | 936 |
| 287 | | | | | 165 | 270 | 1223 | 1207 | 953 | 937 |
| 288 | 0.00025 | 0.00025 | 0.00025 | | 178 | 272 | 1094 | 1006 | 822 | 734 |
| 289 | 0.00125 | 0.00125 | 0.00125 | | 167 | 242 | 800 | 686 | 558 | 444 |
| 290 | 0.0025 | 0.0025 | 0.0025 | | 224 | 212 | 605 | 550 | 393 | 338 |
| 291 | 0.00025 | 0.00025 | 0.00025 | 1 | 171 | 252 | 1039 | 1010 | 787 | 758 |
| 292 | 0.00125 | 0.00125 | 0.00125 | 1 | 260 | 258 | 862 | 872 | 604 | 614 |
| 293 | 0.0025 | 0.0025 | 0.0025 | 1 | 264 | 257 | 242 | 242 | −15 | −15 | was found with addition of sodium lauroyl sarcosinate and superior bioefficacy found with addition of both sodium lauroyl sarcosinate and sodium lauryl sulfate.

Examples 294-325

Antibacterial Study

A series of experiments were conducted to evaluate the performance of the individual components of the claimed bioactive compositions as well as various combinations thereof, including, the claimed compositions themselves, in suppressing the growth of various bacteria. *Escherichia coli* (*E. coli*), *Pseudomonas aeruginosa* (*P. aeruginosa*) and *Staphylococcus aureus* (*S. aureus*) were selected as test organisms as they are generally accepted in the industry as indicator organisms for a wide variety of bacteria. Two different test methodologies were evaluated, one testing the efficacy in a growth broth media and the other testing inhibition in plated growth media.

Examples 309-321

In the first set of experiments a growth medium was prepared by adding 10 grams of nutrient medium (Difco Sabouraud dextrose broth from BD of Franklin Lakes, N.J., USA) to 300 ml of distilled water. The 20 ml aliquots of the growth medium were dispensed into sterile into 40 ml borosilicate glass vials with Teflon lined caps (VWR International Cat. No. 15900-004). The vials were inoculated with the bacteria using a sterile loop and the vials then incubated at 37° C. A bioactive composition according to the invention was then added to certain vials, the bioactive composition was (MI2), as described above, comprising a 16% aqueous citric acid solution having dissolved therein silver citrate, copper citrate and zinc citrate, each added in an amount to provide 200 ppm of each metal, together with 0.25% sodium Lauroyl sarcosinate and 0.32% sodium lauryl sulfate. The turbidity of each mixture was then determined and the vial transferred to an incubator at 30° C. Turbidity measurements were performed as in the above cited yeast studies. Each vial was periodically removed from the incubator and the mixture in the vials assessed for turbidity. The specific formulations tested, the timing for each turbidity evaluation, and the results attained thereby were as set forth in Table 18.

As with the yeast study, the concentration of the metals refers the approximate amount of each metal, copper, silver and zinc. The concentrations do not account for the volume of MI2 added: thus, the concentrations presented are on the basis of a 20 ml total volume.

As seen in Table 18, there was short term increase in turbidity. Since it was not anticipated that any significant growth would have manifested in such a short period of time, it is believed that the initial increase in turbidity resulted from a denaturation of proteins in the broth and/or bacterial proteins. Regardless, the longer term results show excellent bacterial inhibition with the compositions according to the present invention.

TABLE 18

| Example | Bacterium | MI2 (ml) | Metals ppm | T0 | T 0.5 | T 18 | T 24 | T 96 |
|---|---|---|---|---|---|---|---|---|
| 294 | E. coli | 0 | 0 | 15.3 | 16 | 119 | 136 | 264 |
| 295 | | 0.5 | 5 | 131 | 135.3 | 165 | 162 | 162 |
| 296 | | 1 | 10 | 445 | 454 | 481 | 480 | 480 |
| 297 | | 2 | 20 | 1039 | 1080 | 1135 | 1140 | 1009 |
| 298 | p. aeruginosa | 0 | 0 | 35.8 | 37.8 | 158 | 383 | 436 |
| 299 | | 0.5 | 5 | 197 | 207 | 250 | 262 | 261 |
| 300 | | 1 | 10 | 705 | 735 | 782 | 808 | 807 |
| 301 | | 2 | 20 | 1011 | 1057 | 1121 | 1159 | 1146 |
| 302 | S. aureus | 0 | 0 | 46 | 45 | 148 | 184 | 406 |
| 303 | | 0.5 | 5 | 215 | 163 | 173 | 183 | 184 |
| 304 | | 1 | 10 | 643 | 494 | 326 | 309 | 276 |
| 305 | | 2 | 20 | 1203 | 1032 | 595 | 525 | 281 |

Example 306

In this experiment, six 25 mm sterile coverslips were placed into separate 100×15 mm sterile Petri dishes and two of each inoculated with 100 µl of one of three TSB broths: each broth containing one of E. coli, P. aeruginosa and S. aureus that had been allowed to incubate for 48-54 hours. In order to affix the inoculum to the coverslips, the Petri dishes were placed on a low temperature hot plate for approximately 5 minutes. One of each of the inoculated Petri dishes was set aside as positive controls. The other was sprayed with 4 sprays of a 4:1 dilution of the bioactive compositions MI2. After 2-3 minutes the coverslips and liquid contents of each Petri dish was aseptically transferred into separate vials containing 20 ml of TSB and incubated at 37° C. for 24 hours. Negative controls were prepared by placing non-inoculated sterile coverslips into the 20 ml TSB and incubating as well. After 24 hours, no growth was observed with the negative controls or with those inoculated coverslips that had been sprayed with the bioactive composition of the present invention. Visual growth was observed in two of the positive controls (i.e., those vials containing the inoculated coverslips that had not been sprayed): the positive control for P. aeruginosa failed to show visual growth. It is believed that the failure of the later to show growth resulted from overheating the inoculum during the fixturing step.

Example 307

In this experiment, two Trypticase soy agar (TSA) plates were inoculated with 500 µl of one of three TSB broths for a total of 6 inoculated plates: each broth contained one of E. coli, P. aeruginosa and S. aureus that had been allowed to incubate for 48-54 hours. The inoculum was evenly spread across the surface of the plate with a sterile loop. A 15 mm diameter disc of filter paper that had been dipped in a 4:1 dilution of the MI2 bioactive composition was placed in the center of one of each set of inoculated plates and all plates were placed in an incubator at 37° C. for 24 hours. Non-inoculated control plates were also placed in the incubator as well.

After 24 hours, visual growth was observed. No bacterial growth was seen in the non-inoculated plates. Growth was observed on all of the inoculated plates; however, in those plates wherein the treated filter paper had been placed, no growth was seen on or near the filter paper. Each treated fitter paper disc manifested a clear zone of inhibition of bacterial growth.

Example 308

In this experiment, two Trypticase soy agar (TSA) plates were innoculated with 500 µl of one of three TSB broths for a total of 6 inoculated plates: each broth contained one of E. coli, P. aeruginosa and S. aureus that had been allowed to incubate for 48-54 hours. The inoculum was evenly spread across the surface of the plate with a sterile loop. One of each inoculated plates was then sprayed, approximately 24 times, with the 4:1 dilution of the MI2 bioactive composition. The inoculated plates plus a set of plates non-inoculated control plates were placed in an incubator at 37° C. for 24 hours.

After 24 hours, visual growth was observed on inoculated, but untreated plates whereas no bacterial growth was seen in the non-inoculated plates or in those inoculated plates that had been sprayed with the diluted bioactive composition.

Examples 309

Bacterial MIC Study

A study was conducted to determine the minimum inhibitory concentration (MIC) of the MI2 acid solution, i.e., 200 ppm of each of silver, copper and zinc metal (see Examples 72-79). Three different bacteria were evaluated, *Clavibacter michiganese, Pseudomonas syringae* and *Erwinia amylovora*, each in a different growth medium appropriate for that bacteria, namely brain infusion agar/broth, nutrient agar/broth, and nutrient glucose agar/broth, respectively. In conducting the test, three sets of 10 test tubes were prepared, one set for each bacteria, and labeled 1 to 10. 0.5 ml of the appropriate broth was placed in each of test tubes 2 through 10. Then 0.5 ml of the MI2 solution was added to each of test tubes 1 and 2. 0.5 ml of the contents of test tube 2 was then transferred to test tube 3 and then 0.5 ml of test tube 3 to test tube 4 and so on to test tube 9. 0.5 ml or test tube 9 was discarded. A 0.5 ml suspension of each bacteria to be tested was then added to each of the ten tubes for that series and the tubes incubated for 24 hours at 26° C. Because the acid solution caused considerable cloudiness of the tubes to which it was added, macroscopic evaluation was not possible. Instead, each tube was subcultured onto corresponding agar plates. The observed growth was as indicated in Table 19 (a "+" indicates visual growth and a "−" no growth).

TABLE 19

| Test Tube | 1 | 2 | 3 | 4 | 5 | 6 | 7 | 8 | 9 | 10 |
|---|---|---|---|---|---|---|---|---|---|---|
| Metals concentration* (ppm) | 200 | 50 | 25 | 12.5 | 6.75 | 3.125 | 1.56 | 0.782 | 0.391 | 0.195 |
| C. michiganese | − | − | − | − | − | − | + | + | + | + |
| P. syringae | − | − | − | − | − | + | + | + | + | + |
| E. amylovora | − | − | − | − | − | − | + | + | + | + |

*concentration of each metal, the total metal content is 3 time the number presented.

Based on the results presented in Table 19, the MIC of MI2 is 3.125 ppm for *C. michiganese* and for *E. amylovora* and 6.75 ppm for *P. syringae*. The bioefficacy of such low levels are anticipated to show synergy when combined with conventional fungicides/bactericides for these target organisms Example 310

*Alternaria* Leaf Spot

To demonstrate the efficacy of the bioactive compositions on live plants, a comparative study was conducted comparing the efficacy of a bioactive composition according to the present invention to two commercial products, Eagle 40WP, a myclobutanil based (40 wt %) fungicide available from Dow AgroSciences LLC of Indianapolis, Ind., USA, and Scala S.C., a pyrimethanil based (54.6 wt %) fungicide available from Bayer CropScience LP of Research Triangle Park, N.C., USA. Additional evaluations were conducted to assess the potential for synergy between the inventive bioactive compositions and Eagle 40WP. The bioactive composition according to the present invention comprised a 16% aqueous citric acid solution having dissolved therein silver citrate, copper citrate, and zinc citrate in an amount to provide 200 ppm of each metal in the solution, 0.25% sodium lauroyl sarcosinate and 0.32% sodium lauryl sulfate (MI6). This solution was diluted at rates of 40:1 and 20:1 for application to the plants thereby providing a solution containing ~5 ppm and ~10 ppm of each metal as sprayed.

*Pittosporum tobira* "Wheeleri" rooted cuttings were planted in standard 4 inch pots containing Sunshine Mix No. 1 and fertilized with ½ tsp. Osmocote Plus 15-9-12. The plants were placed in a heated greenhouse with poly and shade cloth covering the top and sides and flood irrigated as needed. After 44 days, the plants were treated with the various antifungal treatments—12 plants were treated with each treatment. Thereafter, the plants were placed in individual clear plastic bags (high humidity) in the greenhouse for the duration of the study. The plants were irrigated from below using an ebb and flood bench to assure no water application to their leaves during the trial. The plants were subsequently inoculated by spraying with a spore suspension of a culture of *Altemaria pittospori* mixed with sterilized water 4 days following the initial treatment. The treatments were reapplied 7 days and 17 days following inoculation. All treatments were applied by spray until the surfaces of the plant leaves were fully wetted (began to drip). Two sets of plants were used as positive and negative controls: the first set was treated with water only (Treatment A) and not inoculated. The second set was also treated with water only, but was also inoculated concurrent with the others. The specific formulations for each of the treatments were as set forth in Table 20.

TABLE 20

| Treatment | Composition | Dilution |
|---|---|---|
| A | Water - noninoculated | |
| B | Water - inoculated | |
| C | MI6 | 6.25 ml/250 ml water |
| D | MI6 | 12.5 ml/250 ml water |
| E | MI6/Eagle 40WP | 6.25 ml/250 ml water// 1.5 oz/100 gal water |
| F | MI6/Eagle 40WP | 6.25/250 ml water// 3.0 oz/100 gal water |
| G | MI6/Eagle 40 WP | 12.5 ml/250 ml water// 1.5 oz/100 gal water |
| H | Eagle 40 WP | 1.5* oz/100 gal water |
| I | Eagle 40WP | 3.0 oz/100 gal water |
| J | Scala | 9.0* oz/100 gal water |

*manufacturer recommended application rates

Six days following the second treatment, the plants were evaluated for *Alternaria* leaf spot by visual inspection. The results of the leaf spot evaluation were as presented in Table 21. As seen in Table 21, those plants treated with the lowest concentration of the bioactive composition (with ~5 ppm of each metal ion—Treatment C) still showed nearly a 50% drop in leaf spot formation. Doubling the bioactive composition (~10 ppm of each metal ion—Treatment D) reduced leaf spot by over 75%. Somewhat similar results were found with the two dilutions of the commercial fungicide Eagle 40WP with the lower concentration (Treatment H) reducing leaf spot by about 30% while the higher concentration (Treatment I)

reduced leaf spot by 80%. Combining the two provided marked improvement with, oddly enough, the combination of the two lowest concentrations providing nearly complete inhibition of leaf spot manifestation. The other commercial fungicide Scala SC provided no inhibition and, appeared to promote the manifestation of leaf spot.

TABLE 21

| Treat-ment | Plant No. | | | | | | | | | | | | Mean |
|---|---|---|---|---|---|---|---|---|---|---|---|---|---|
| | 1 | 2 | 3 | 4 | 5 | 6 | 7 | 8 | 9 | 10 | 11 | 12 | |
| A. | 0 | 0 | 0 | 0 | 0 | 0 | 0 | 0 | 0 | 0 | 0 | 0 | 0.0 |
| B. | 4 | 5 | 0 | 15 | 35 | 20 | 40 | 15 | 10 | 25 | 30 | 20 | 18.2 |
| C. | 0 | 0 | 0 | 0 | 0 | 5 | 35 | 35 | 40 | 0 | 0 | 0 | 9.6 |
| D. | 0 | 1 | 0 | 0 | 5 | 0 | 0 | 0 | 0 | 5 | 10 | 30 | 4.2 |
| E. | 0 | 0 | 0 | 0 | 0 | 1 | 0 | 0 | 5 | 0 | 0 | 0 | 0.5 |
| F. | 0 | 0 | 0 | 0 | 0 | 0 | 25 | 0 | 0 | 5 | 10 | 0 | 3.3 |
| G. | 0 | 0 | 0 | 0 | 0 | 0 | 0 | 15 | 10 | 0 | 0 | 0 | 2.1 |
| H. | 0 | 0 | 0 | 5 | 10 | 0 | 30 | 35 | 40 | 10 | 10 | 15 | 12.9 |
| I. | 2 | 0 | 0 | 0 | 0 | 0 | 10 | 25 | 5 | 0 | 0 | 0 | 3.5 |
| J. | 25 | 25 | 10 | 5 | 15 | 25 | 30 | 0 | 40 | 40 | 40 | 20 | 22.9 |

Eleven days following the last treatment, disease severity was once again assessed. However, owing to the number of spots which made giving a numerical assessment impossible, disease severity was recorded using the following scale: 1-1—no disease, 2—slight, 3—moderate, 4—severe to 5—plant dead. The results are presented in Table 22.

TABLE 22

| Treat-ment | Plant No. | | | | | | | | | | | | Mean |
|---|---|---|---|---|---|---|---|---|---|---|---|---|---|
| | 1 | 2 | 3 | 4 | 5 | 6 | 7 | 8 | 9 | 10 | 11 | 12 | |
| A. | 2 | 1 | 1 | 1 | 1 | 1 | 1 | 1 | 1 | 1 | 1 | 1 | 1.1 a |
| B. | 2.5 | 2.5 | 1 | 4 | 3.5 | 3 | 4 | 2 | 2 | 3 | 3 | 3.5 | 2.8 c |
| C. | 1 | 1 | 1 | 1 | 1 | 2 | 2 | 2.5 | 2.5 | 2 | 2 | 1 | 1.6 a |
| D. | 1 | 1 | 2 | 1 | 2 | 1 | 1 | 1 | 1 | 1 | 2 | 2.5 | 1.4 a |
| E. | 1 | 1 | 1 | 1 | 1 | 1 | 2 | 1 | 1 | 1 | 1 | 2 | 1.2 a |
| F. | 1 | 2 | 2 | 1 | 1 | 1 | 2 | 1 | 1 | 1 | 2 | 1 | 1.3 a |
| G. | 1 | 1 | 1 | 1 | 1 | 1 | 2 | 2 | 2 | 1 | 1 | 1 | 1.2 a |
| H. | 2 | 2 | 1 | 2.5 | 2 | 2 | 2.5 | 3 | 3 | 2 | 2.5 | 2.5 | 2.2 b |
| I. | 2.5 | 1 | 1 | 1 | 2 | 2 | 2 | 2 | 1 | 2 | 2 | 2 | 1.7 a |
| J. | 3.5 | 4 | 3 | 3 | 3 | 4 | 3.5 | 2.5 | 4 | 4 | 4 | 4 | 3.5 d |

As shown in Table 22, the bioactive compositions according to the present invention provided excellent protection against leaf spot, with those plants treated at the higher level and in combination with the commercial fungicide Eagle 40WP showing nearly the same level of disease as those that had not been inoculated at all. On the contrary, the Eagle alone, even at the recommended application rate, proved less efficacious than the bioactive composition. Finally, the Scala once again failed to show any efficacy and, in fact, proved more detrimental. It was suspected that the Scala treated plants manifested both leaf spot disease and phytotoxicity. None of the plants treated with the bioactive composition or the commercial Eagle fungicide showed evidence of phytotoxicity.

Example 311

Fire Blight on Crabapples

A study of the bioefficacy of the various agrichemical compositions, including bioactive acid solutions and blends thereof with an antibiotic agrichemical, were evaluated to assess their bioefficacy against fire blight on crabapples. The study was conducted on 5 year old Snow Drift crabapple trees, with each of the compositions being applied to ten trees in two-subplots of five trees, four different times: at 100% bloom—day 1, a second application was made on day 4, a third on day 11 and a final treatment on day 19. The trees were inoculated with $E.\ amylovora$ 153N at a concentration of $4 \times 10^6$ cells per milliliter on day 1, following drying of the treatment, with the inoculation being repeated on day 13. Evaluation for fire blight was completed on 100 blossoms for each of the subplots on day 12, day 19 and day 27. Additionally, the incidence of shoot infection and the length of cankers were evaluated on day 63. The results are shown in Table 23.

The test compositions were prepared by forming solutions of the bioactive agents. Two different dilutions of the MI2 bioactive were evaluated, the first employing 94.46 ml/gallon (25 ml/l) of water (5 ppm of each metal) and the second 188.9 ml/gallon (50 ml/l) of water (10 ppm of each metal). A streptomycin product (17% concentrated) was diluted at a rate of 0.049 lbs/gallon (58.72 g/l) (200 ppm). Finally, copper hydroxide was diluted at a rate of 1 lb/gallon (119.8 g/l). Each of the compositions and blends were spray applied at a rate of 50 gallons (189.3 l) pre acre. The specific tests and the results attained therewith are shown in Table 23. The results are presented as the mean of the counts.

As seen in Table 23, all tested compositions showed fewer infected flowers as compared to the control. The combination of the MI2 acid solution with streptomycin performed better than either bioactive alone. A significant rate response was seen between the two MI2 compositions: the 10 ppm solution performing significantly better than the 5 ppm solution. Shoot blight incidence was greatly reduced for the copper hydroxide, streptomycin an streptomycin/MI2 combination and a modest improvement with the higher concentrated solution of MI2. Only streptomycin and copper hydroxide appeared to prevent canker, while measurable cankers were noted with all compositions containing bioactive acid solution. Even so, these results show a marked benefit of the bioactive acid solutions alone or in combination with streptomycin. More importantly, it must be noted that even at the higher concentration MI2 composition, the 10 ppm of each metal, a total of 30 ppm metals, pales in comparison to the more than 50,000 ppm copper in the copper hydroxide solution. In essence, each application of the copper hydroxide release almost 1000 g or Copper into the environment compared to less than 2 grams or any one metal released by higher concentration MI2 composition.

TABLE 23

| Bioactive | Rate (per acre) | Blossom Incidence Day | | | Shoot Incidence Day | Canker Size (cm) |
|---|---|---|---|---|---|---|
| | | 12 | 19 | 27 | 63 | 63 |
| MI2[a] | 4.723 l/a | 0.2 | 5.5 | 16.5 | 8.8 | 40.0 |
| MI2 | 9.445 l/a | 1.7 | 2.2 | 6.0 | 4.8 | 19.8 |
| Copper Hydroxide[b] | 5 lbs/a (2.27 kg/a) | 3.1 | 2.2 | 9.0 | 1.0 | 0.0 |
| Streptomycin[c] | 0.49 lb/a | 1.8 | 4.8 | 3.09 | 1.2 | 0.0 |
| MI2 + Streptomycin | 4.723/a 0.49 lbs/a | 1.3 | 1.7 | 4.3 | 1.0 | 26.0 |
| Control (untreated) | — | 7.0 | 8.5 | 31.7 | 7.6 | 22.4 |

[a]16% w/w aqueous citric acid solution having dissolved therein silver citrate, copper citrate and zinc citrate, each added in an amount to provide 200 ppm of each metal, together with 0.25% sodium Lauroyl sarcosinate and 0.32% sodium lauryl sulfate.
[b]53% w/w concentrated copper hydroxide
[c]17% w/w streptomycin Although the present invention has been described with respect to the foregoing specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles.

The invention claimed is:

1. A bioactive agrichemical concentrate comprising a) at least one carboxylic acid selected from citric acid, valeric acid, itaconic acid, acetic, citriconic acid, lactic acid, malic acid, succinic acid, aldaric acid, proprionic acid, malonic acid, maleic acid, salicylic acid, glutaric acid, tartaric acids, and benzoic acid, b) at least one antimicrobial metal ion or ion source wherein the antimicrobial metal ions or the antimicrobial metal ions of the ion source are selected from the group consisting of silver, a combination of silver and zinc, a combination of silver and copper and a combination of silver, copper and zinc, and c) optionally, at least one surfactant; wherein the acid is present at a level of at least 40 weight percent and in a molar excess relative to the metal ions of at least 2 times; said concentrate being free of other bioactive agrichemical actives in an amount which manifests efficacious or synergistic activity or manifests synergy with the metal/acid antifungal active of said concentrate when said concentrate is in a diluted form said diluted form comprising i) the acid is from 0.01 to 20 weight percent; ii) the amount of antimicrobial metal ion is 500 ppm or less in the case of a single metal ion or 1000 ppm or less in the case of multiple metal ions, iii) the concentration of the surfactant, if present, is 0.001 to about 3 weight percent, and iv) the pH of the dilute solution when diluted in purified water is at least 2 and less than 6; said concentrate in said diluted form being synergistically effective for killing, controlling and/or inhibiting the growth of fungi on plants when applied to the soil in which a seed, crop or plant is or is to be planted; to the aqueous environment in which plants are growing; or to plants in their growing environment.

2. The concentrate of claim 1 wherein the concentrate is an intimate, mixture of the recited ingredients.

3. The concentrate of claim 1 wherein the acid is B present in an amount of from 40 weight percent to 80 weight percent based on the weight of the concentrate.

4. The concentrate of claim 1 wherein the carboxylic acid is selected from the group consisting of citric acid, salicylic acid, glutaric acid and tartaric acid.

5. The concentration of claim 1 wherein the concentrate is in the form of a liquid.

6. The concentrate of claim 1 wherein the concentrate is in the form of a solid.

7. The concentrate of claim 6 wherein the solid is a flowable powder or granular mixture.

8. The concentrate of claim 1 wherein the concentrate is to be diluted with water or an aqueous based solution.

9. The concentrate of claim 1 wherein the concentrate is to be diluted with a solid filler or solid carrier material.

10. The concentrate of claim 1 wherein the rate of dilution is to be from 10:1 to at least 200:1, diluent to concentrate.

11. The concentrate of claim 1 wherein the rate of dilution is to be from 80:1 to 200:1, diluent to concentrate.

12. The concentrate of claim 1 wherein the acid of the bioactive acid composition is present in at least a 5 times molar excess relative to the metal ion(s).

13. The concentrate of claim 1 wherein the antimicrobial metal ions are selected from the group consisting of a combination of silver and copper ions and a combination of silver and zinc ions.

14. The concentrate of claim 1 wherein at least one anionic, non-ionic and/or amphoteric surfactant is present.

15. The concentrate of claim 14 wherein a combination of two or more surfactants is employed, each surfactant independently selected from the group consisting of sulfonates, sulfates, sulfosuccinates, sarcosinates, mono- and di-glycerides, amine oxides, ether carboxylates, betaines, sulfobetaines, and glycinates.

16. The concentrate of claim 14 wherein the surfactants are independently selected from the group consisting of sulfonates, sulfates, sulfosuccinates, sarcosinates, and amine oxides.

17. The concentrate of claim 1 wherein the pH is from 2 to 5 in the diluted state.

18. The concentrate of claim 1 wherein in the diluted state the acid is present at a level of from about 0.1 to about 4 weight percent and the antimicrobial ion is present at a concentration of from about 1 ppm to about 300 ppm in the case of a single metal ion and from about 2 to about 500 in the case of multiple metal ions.

19. The concentrate of claim 1 wherein in the diluted state the acid is present at a level of from about 0.1 to about 4 weight percent and the antimicrobial is present at a concentration of from about 2 ppm to about 100 ppm in the case of a single antimicrobial metal ion and from about 2 ppm to about 300 ppm in the case of multiple antimicrobial metal ions.

20. The concentrate of claim 1 wherein in the diluted state the acid is present at a level of from about 0.1 to about 4 weight percent and the antimicrobial is present at a concentration of from about 5 ppm to about 50 ppm in the case of a single antimicrobial metal ion and from about 5 ppm to about 150 ppm in the case of multiple antimicrobial metal ions.

21. The concentrate of claim 1 wherein the composition is free of phosphoric acid.

22. The concentrate of claim 1 wherein the composition is free of mineral acids.

23. The concentrate of claim 1 wherein the at least one antimicrobial metal ion is a combination of silver, copper and zinc ions.

* * * * *